(12) United States Patent
Bongiorni et al.

(10) Patent No.: US 10,287,591 B2
(45) Date of Patent: May 14, 2019

(54) ENHANCED PROTEIN EXPRESSION

(71) Applicant: DANISCO US INC., Palo Alto, CA (US)

(72) Inventors: Cristina Bongiorni, Fremont, CA (US); Rei Otsuka, San Mateo, CA (US); Brian F. Schmidt, Half Moon Bay, CA (US); Anita Van Kimmenade, Woodside, CA (US)

(73) Assignee: DANISCO US INCCA (US)

( * ) Notice: Subject to any disclaimer, the term of this patent is extended or adjusted under 35 U.S.C. 154(b) by 0 days.

(21) Appl. No.: 15/108,074

(22) PCT Filed: Dec. 8, 2014

(86) PCT No.: PCT/US2014/069019
§ 371 (c)(1),
(2) Date: Jun. 24, 2016

(87) PCT Pub. No.: WO2015/102814
PCT Pub. Date: Jul. 9, 2015

(65) Prior Publication Data
US 2016/0319288 A1    Nov. 3, 2016

Related U.S. Application Data

(60) Provisional application No. 61/922,613, filed on Dec. 31, 2013.

(51) Int. Cl.
*C12N 15/75*     (2006.01)
*C07K 14/32*     (2006.01)

(52) U.S. Cl.
CPC .............. *C12N 15/75* (2013.01); *C07K 14/32* (2013.01)

(58) Field of Classification Search
None
See application file for complete search history.

(56) References Cited

U.S. PATENT DOCUMENTS

| | | |
|---|---|---|
| 4,302,544 A | 11/1981 | Young et al. |
| 4,450,235 A | 5/1984 | Dean et al. |
| 4,683,195 A | 7/1987 | Mullis et al. |
| 4,683,202 A | 7/1987 | Mullis |
| 4,760,025 A | 7/1988 | Estell et al. |
| 4,914,031 A | 4/1990 | Zukowski et al. |

(Continued)

FOREIGN PATENT DOCUMENTS

| | | |
|---|---|---|
| EP | 0134048 A1 | 3/1985 |
| EP | 0414279 B1 | 11/1993 |

(Continued)

OTHER PUBLICATIONS

Amoroso et al., PLOS Pathogens, 8 (3): e1002571, 2012, pp. 1-6.*

(Continued)

*Primary Examiner* — Nancy A Treptow

(57) ABSTRACT

The present invention relates in general to bacterial cells having a genetic alteration that results in increased expression of a protein of interest and methods of making and using such cells. Aspects of the present invention include Gram positive microorganisms, such as *Bacillus* species, having a genetic alteration that modifies activity of a protein encoded by the ykf operon and results in enhanced expression of a protein of interest.

15 Claims, 7 Drawing Sheets

Specification includes a Sequence Listing.

(56) References Cited

U.S. PATENT DOCUMENTS

| | | | |
|---|---|---|---|
| 4,965,188 | A | 10/1990 | Mullis et al. |
| 4,980,288 | A | 12/1990 | Bryan et al. |
| 5,208,158 | A | 5/1993 | Bech et al. |
| 5,217,878 | A | 6/1993 | van Eekelen et al. |
| 5,264,366 | A | 11/1993 | Ferrari et al. |
| RE34,606 | E | 5/1994 | Estell et al. |
| 5,310,675 | A | 5/1994 | Estell et al. |
| 5,322,770 | A | 6/1994 | Gelfand |
| 5,336,611 | A | 8/1994 | van Eekelen et al. |
| 5,399,283 | A | 3/1995 | Stabinsky et al. |
| 5,482,849 | A | 1/1996 | Branner et al. |
| 5,631,217 | A | 5/1997 | Branner et al. |
| 5,665,587 | A | 9/1997 | Aaslyng et al. |
| 5,700,676 | A | 12/1997 | Bott et al. |
| 5,741,694 | A | 4/1998 | Hastrup et al. |
| 5,858,757 | A | 1/1999 | Von Der Osten et al. |
| 5,880,080 | A | 3/1999 | Amory et al. |
| 6,197,567 | B1 | 3/2001 | Aaslyng et al. |
| 6,218,165 | B1 | 4/2001 | Estell et al. |

FOREIGN PATENT DOCUMENTS

| | | | |
|---|---|---|---|
| WO | | 89/06279 A1 | 7/1989 |
| WO | | 99/20726 A1 | 4/1999 |
| WO | | 99/20769 A2 | 4/1999 |
| WO | | 99/20770 A2 | 4/1999 |
| WO | | 2003/070963 A2 | 8/2003 |
| WO | WO 2008/066931 | * | 6/2008 |
| WO | | 2010/144283 A1 | 12/2010 |

OTHER PUBLICATIONS

Aunstrup et al., "Proteases from Alkalophilic *Bacillus Species*," In. Proc. IV IFS: Ferment. Technol. Today, 1972, pp. 299-305.
Arigoni et al., "The SpoIIE phosphatase, the sporulation septum and the establishment of forespore-specific transcription in Bacillus subtilis: a reassessment," Mol. Microbiol., 1999, vol. 31, No. 5, pp. 1407-1415.
Amoroso al., "A Petidoglycan Fragment Triggers Beta-lactam Resistance in Bacillus licheniformis," Plos Pathogens, 2012, vol. 8, No. 3, pp. 1-15.
Altschul et al., "Local Alignment Statistics," in Meth. Enzymol., 1996, vol. 266, Chapter 27, pp. 460-480.
Altschul et al., "Basic Local Alignment Search Tool," 1990, J. Mol. Biol., vol. 215, pp. 403-410.
Zukowski, "Production of commercially valuable products," In Biology of Bacilli: Applications to Industry, 1992, Chapter 11, pp. 311-337, Doi et al., (Eds.), Butterworth-Heinemann, Stoneham, MA.
Wu et al., "The Ligation Amplification Reaction (LAR)-Amplification of Specific DNA Sequences Using Sequential Rounds of Template-Dependent Ligation," Genomics, 1989, vol. 4, pp. 560-569.
Wells et al., "Cloning, sequencing, and secretion of Bacillus amyloliquefaciens subtilisin in Bacillus subtilis," Nucleic Acids Res., 1983, vol. 11, pp. 7911-7925.
Ward, "Proteinases," In Microbial Enzymes and Biotechnology, 1983, Chapter 6, pp. 251-317, Fogarty, (Ed.), Applied Science, London.
Wang et al., "Expression and secretion of human atrial natriuretic alpha-factor in Bacillus subtilis using the subtilisin signal peptide," Gene, 1988, vol. 69, pp. 39-47.
Vorobjeva et al., "Transformation of Bacillus Megaterium Protoplasts by Plasmid DNA," FEMS Microbial. Lett., 1980, vol. 7, pp. 261-263.
Vasantha et al., "Genes for Alkaline Protease and Neutral Protease from Bacillus amyloliquefaciens Contain a Large Open Reading Frame Between the Regions Coding for Signal Sequence and Mature Protein," J. Bacteriol., 1984, vol. 159, pp. 811-819.

Thompson et al., "Clustal W: improving the sensitivity of progressive multiple sequence alignment through sequence weighting, position-specific gap penalties and weight matrix choice," Nucleic Acids Res., 1994, vol. 22, pp. 4673-4680.
Stahl et al., "Replacement of the Bacillus subtilis Subtilisin Structural Gene with an In Vitro-Derived Deletion Mutation," J. Bacteriol., 1984, vol. 158, pp. 411-418.
Smith et al., "Protoplast Transformation in Coryneform Bacteria and Introduction of an alpha-Amylase Gene from Bacillus amyloliquefaciens into Brevibacterium lactofermentum," Appl. Env. Microbiol., 1986, vol. 51, pp. 634-639.
Smith et al., "Comparison of Biosequences,"Adv. Appl. Math., 1981, vol. 2, pp. 482-489.
Shpaer, "GeneAssist: Smith-Waterman and other database similarity searches and identification of motifs," In Methods Mol. Biol., 1997, vol. 70, pp. 173-187.
Saunders et al., "Use of Chromosomal Integration in the Establishment and Expression of blaZ, a *Staphylococcus aureus* J3-Lactamase Gene, in Bacillus subtilis," J. Bacteriol., 1984, vol. 157, pp. 718-726.
Priest, "Extracellular Enzyme Synthesis in the Genus Bacillus," Bacterial. Rev., 1977, vol. 41, pp. 711-753.
Perego, "Integrational Vectors for Genetic Manipulation in Bacillus subtilis," In Bacillus subtilis and Other Gram-Positive Bacteria, Sonenshein et al., (Eds.), 1993, Chapter 42, pp. 615-624, American Society for Microbiology, Washington, DC.
Perego et al., "The oligopeptide transport system of Bacillus subtilis plays a role in the initiation of sporulation," Mol. Microbiol., 1991, vol. 5, pp. 173-185.
Pearson et al., "Improved tools for biological sequence comparison," Proc. Natl. Acad. Sci. USA, 1988, vol. 85, pp. 2444-2448.
PCT International Searach Report and the Written Opinion of the International Searching Authority for Application No. PCT/US2014/069019; Marchesini, Patrizia, ISA; ISA/EP; dated Mar. 12, 2015.
Palva, "Molecular cloning of a-amylase gene from Bacillus amyloliquefaciens and its expression in B. subtilis," Gene, 1982, vol. 19, pp. 81-87.
Palmeros et al., "A family of removable cassettes designed to obtain antibiotic-resistance-free genomic modifications of *Escherichia coli* and other bacteria," Gene, 2000, vol. 247, pp. 255-264.
Olmos et al., "Effects of the sinR and degU32 (Hy) mutations on the regulation of the aprE gene in Bacillus subtilis," Mol. Gen. Genet., 1997, vol. 253, pp. 562-567.
Needleman et al., "A General Method Applicable to the Search for Similarities in the Amino Acid Sequence of Two Proteins," J. Mol. Biol., 1970, vol. 48, pp. 443-453.
Msadek et al., "Signal Transduction Pathway Controlling Synthesis of a Class of Degradative Enzymes in Bacillus subtilis: Expression of the Regulatory Genes and Analysis of Mutations in degS and degU," J. Bacteriol., 1990, vol. 172, pp. 824-834.
Morinaga et al., "Improvement of oligonucleotide-directed site-specific mutagenesis using double-stranded plasmid DNA," Biotech., 1984, vol. 2, pp. 636-639.
McDonald, et al., "Plasmid Transformation of Bacillus sphaericus 1593," J. Gen. Microbiol., 1984, vol. 130, pp. 203-208.
Mann et al., "Transformation of *Bacillus* spp.: an Examination of the Transformation of Bacillus Protoplasts by Plasmids pUBII0 and pHV33," Current Microbiol., 1986, vol. 13, pp. 191-195.
Maddox et al., "Elevated Serum Levels in Human Pregnancy of a Molecule Immunochemically Similar to Eosinophil Granule Major Basic Protein," J. Exp. Med., 1983, vol. 158, pp. 1211-1226.
Kuhn et al., "Cre/loxP Recombination System and Gene Targeting," In Methods in Molecular Biology—Transgenesis Techniques Priniciples and Protocols, Second Edition, Clarke (Ed.), vol. 180, Chapter 9, pp. 175-204.
Kramer et al., "The gapped duplex DNA approach to oligonucleotide-directed mutation construction," Nucleic Acids Res., 1984, vol. 12, pp. 9441-9456.
Karlin et al., "A Replicating RNA Molecule Suitable for a Detailed Analysis of Extracellular Evolution and Replication," Proc. Natl. Acad. Sci. USA, 1993, vol. 90, pp. 5873-5877.

(56) References Cited

OTHER PUBLICATIONS

Kacian et al., "A Replicating RNA Molecule Suitable for a Detailed Analysis of Extracellular Evolution and Replication," Proc. Natl. Acad. Sci. USA, 1972, vol. 69, pp. 3038-3042.

Hsia et al., "Active-Site Titration of Serine Proteases Using a Fluoride Ion Selective Electrode and Sulfonyl Fluoride Inhibitors,"Anal. Biochem., 1996, vol. 242, pp. 221-227.

Holubova et al., "Transfer of Liposome-Encapsulated Plasmid DNA to Bacillus subtilis Protoplasts and Calcium-Treated *Escherichia coli* Cells," Folia Microbiol., 1985, vol. 30, pp. 97-100.

Hoch et al., "Transformation and Transduction in Recombination-defective Mutants of Bacillus subtilis," J. Bacteriol., 1967, vol. 93, pp. 1925-1937.

Hoch et al., "Chromosomal location of pleitotropic negative sporulation mutations in Bacillus subtilis," Genetics, 1973, vol. 73, pp. 215-228.

Higgins et al., "Fast and sensitive multiple sequence alignments on a microcomputer," CABIOS, 1989 vol. 5, pp. 151-153.

Fischer et al., "Introduction of plasmid pC194 into Bacillus thuringiensis by protoplast transformation and plasmid transfer," Arch. Microbiol., 1984, vol. 139, pp. 213-217.

Ferrari et al., "Genetics," In Bacillus, 1989, Harwood et al. (ed.), Bacillus, Plenum Publishing Corp., pp. 57-72.

Feng et al., "Progressive Sequence Alignment as a Prerequisite to Correct Phylogenetic Trees," J. Mol. Evol., 1987, vol. 35, pp. 351-360.

Fahnestock et al., "Expression of the Staphylococcal Protein A Gene in Bacillus subtilis by Gene Fusions Utilizing the Promoter from a Bacillus amyloliquefaciens alpha-Amylase Gene," J. Bacteriol., 1986, vol. 165, No. 3, pp. 796-804.

Devereux et al., "A comprehensive set of sequence analysis programs for the VAX," Nucl. Acid Res., 1984, vol. 12, pp. 387-395.

Dayhoff et al., "A Model of Evolutionary Change in Proteins," In Atlas of Protein Sequence and Structure 5: Suppl. 3, 1978, pp. 345-352, National Biomedical Research Foundation, Washington, D.C.

Christianson et al., "Peptide Mapping of Subtilisins as a Practical Tool for Locating Protein Sequence Errors during Extensive Protein Engineering Projects," Anal. Biochem., 1994, vol. 223, pp. 119-129.

Chang et al., "High Frequency Transformation of Bacillus subtilis Protoplasts by Plasmid DNA," Mol. Gen. Genet., 1979, vol. 168, pp. 111-115.

Chamberlain et al., "New RNA Polymerase from *Escherichia coli* infected with Bacteriophage T7," Nature, 1970, vol. 228, pp. 227-231.

Caldwell et al., "Correlation between Bacillus subtilis scoC Phenotype and Gene Expression Determined Using Microarrays for Transcriptome Analysis," J. Bacteriol., 2001, vol. 183, pp. 7329-7340.

Bergmeyer et al., (Ed.), "Peptidases, Proteinases and their Inhibitors," In Methods of Enzymatic Analysis, 1984, vol. 5, Verlag Chemie, Weinheim (Book Not Included).

\* cited by examiner

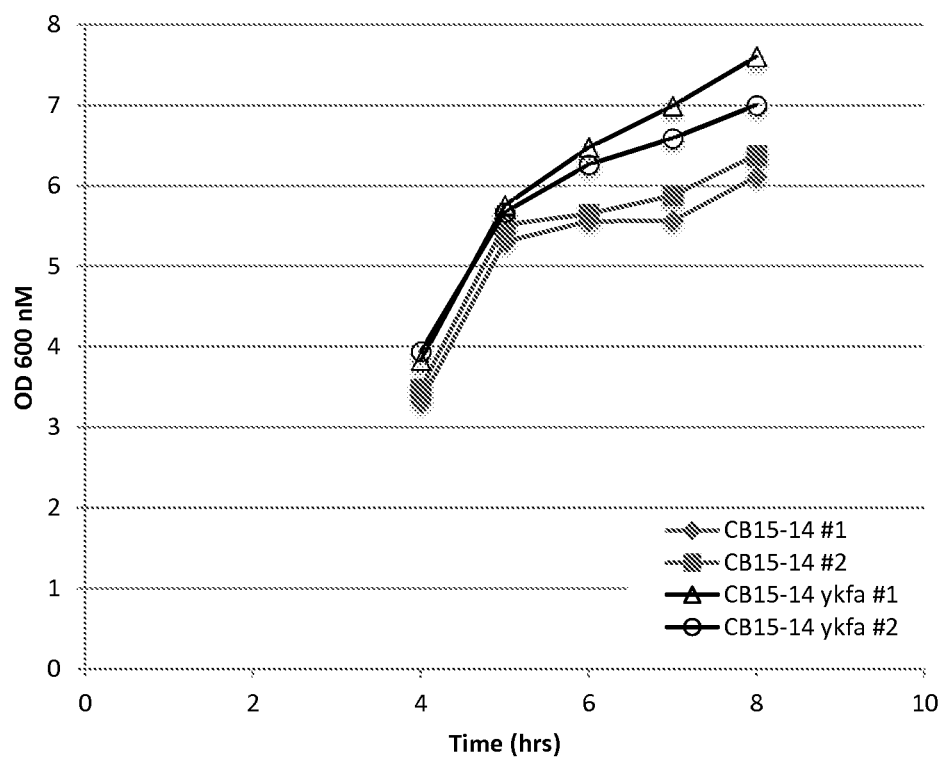

ENHANCED PROTEIN EXPRESSION

CROSS REFERENCE TO RELATED APPLICATIONS

This application is the National Stage of International Application No. PCT/US2014/069019, filed Dec. 8, 2014, which claims benefit of priority from U.S. Provisional Patent Application No. USSN 61/922,613, filed Dec. 31, 2013, the contents of which are incorporated herein by reference in their entirety.

SEQUENCE LISTING

The sequence listing submitted via EFS, in compliance with 37 C.F.R. § 1.52(e), is incorporated herein by reference. The sequence listing text file submitted via EFS contains the file "NB40354USPCT_SequenceListing.txt" created on Sep. 26, 2016, which is 17.1 KB (17,605 bytes) in size.

FIELD OF THE INVENTION

The present invention relates in general to bacterial cells having a genetic alteration that results in increased expression of a protein of interest and methods of making and using such cells. Aspects of the present invention include Gram-positive microorganisms, such as Bacillus species, having a genetic alteration that modifies the activity of a protein encoded by the ykf operon and results in enhanced expression of a protein of interest.

BACKGROUND OF THE INVENTION

Genetic engineering has allowed the improvement of microorganisms used as industrial bioreactors, cell factories and in food fermentations. Gram-positive organisms, including a number of Bacillus species, are used to produce a large number of useful proteins and metabolites (see, e.g., Zukowski, "Production of commercially valuable products," In: Doi and McGlouglin (eds.) Biology of Bacilli: Applications to Industry, Butterworth-Heinemann, Stoneham. Mass. pp 311-337 [1992]). Common Bacillus species used in industry include B. licheniformis, B. amyloliquefaciens and B. subtilis. Because of their GRAS (generally recognized as safe) status, strains of these Bacillus species are natural candidates for the production of proteins utilized in the food and pharmaceutical industries. Examples of proteins produced in Gram-positive organisms include enzymes, e.g., α-amylases, neutral proteases, and alkaline (or serine) proteases.

In spite of advances in the understanding of production of proteins in bacterial host cells, there remains a need for to develop new recombinant strains that express increased levels of a protein of interest.

SUMMARY OF THE INVENTION

The present invention provides recombinant Gram positive cells that express increased levels of a protein of interest and methods of making and using the same. In particular, the present invention relates to bacterial cells having a genetic alteration that results in increased expression of a protein of interest as compared to bacterial cells that do not have the genetic alteration. Aspects of the present invention include Gram-positive microorganisms, such as Bacillus species, having a genetic alteration that modifies the activity of one or more proteins encoded by the ykf operon and results in enhanced expression of a protein of interest. Methods of making and using such recombinant bacterial cells are also provided.

Aspects of the invention include a method for increasing expression of a protein of interest from a Gram positive bacterial cell comprising: a) obtaining an altered Gram positive bacterial cell capable of producing a protein of interest, wherein said altered Gram positive bacterial cell comprises at least one genetic alteration that modifies activity of one or more proteins encoded by the ykf operon; and b) culturing said altered Gram positive bacterial cell under conditions such that said protein of interest is expressed by said altered Gram positive bacterial cell, wherein expression of said protein of interest is increased in said altered Gram positive bacterial cell compared to the expression of said protein of interest in a corresponding unaltered Gram positive bacterial cell grown under essentially the same culture conditions.

In certain embodiments, the altered Gram positive bacterial cell is a Bacillus sp. strain (e.g., Bacillus sp. strain is selected from the group consisting of: B. licheniformis, B. lentus, B. subtilis, B. amyloliquefaciens, B. brevis, B. stearothermophilus, B. alkalophilus, B. coagulans, B. circulans, B. pumilus, B. lautus, B. clausii, B. megaterium, and B. thuringiensis). In certain embodiments, the Bacillus sp. strain is a B. subtilis strain. In certain embodiments, the altered Gram positive bacterial cell further comprises a mutation in a gene selected from the group consisting of degU, degQ, degS, scoC4, spoIIE, and oppA. In certain embodiments, the mutation is degU(Hy)32.

In certain embodiments, the altered Gram positive bacterial cell has reduced activity of the YkfA protein as compared to the activity of the YkfA protein in a corresponding unaltered Gram positive bacterial cell grown under essentially the same culture conditions. In certain embodiments, the altered Gram positive bacterial cell has increased activity of the YkfA protein as compared to the activity of the YkfA protein in a corresponding unaltered Gram positive bacterial cell grown under essentially the same culture conditions.

In certain embodiments, the genetic alteration is in the ykfA gene of said ykf operon. In some embodiments, the genetic alteration is in the endogenous ykfA gene of the ykf operon. In certain embodiments, the ykfA gene is at least 60% identical to SEQ ID NO:1. In certain embodiments, the genetic alteration results in an alteration in an amino acid at a position corresponding to amino acid 252 or 253 of SEQ ID NO: 2. In certain embodiments, the genetic alteration results in an alteration in an amino acid at a position corresponding to amino acids 252 and 253 of SEQ ID NO: 2. In certain embodiments, the genetic alteration results in an alteration in an amino acid at a position corresponding to amino acids 252 and 253 of SEQ ID NO: 2. In certain embodiments, the genetic alteration results in a P to L alteration in an amino acid at a position corresponding to amino acid 252 of SEQ ID NO: 2 (shown in SEQ ID NO: 4). In certain embodiments, the genetic alteration results in a V to L alteration in an amino acid at a position corresponding to amino acid 253 of SEQ ID NO: 2 (shown in SEQ ID NO: 4). In certain embodiments, genetic alterations result in a P to L alteration in an amino acid position corresponding to amino acid 252 and in a V to L alteration in an amino acid position corresponding to amino acid 253 of SEQ ID NO: 2 (shown in SEQ ID NO: 4).

In certain embodiments, the protein of interest is a homologous protein. In certain embodiments, the protein of interest is a heterologous protein. In certain embodiments, the protein of interest is an enzyme. In certain embodiments, the enzyme is selected from the group consisting of: protease, cellulase, pullulanase, amylase, carbohydrase, lipase, isomerase, transferase, kinase, and phosphatase. In certain embodiments, the protein of interest is a protease. In certain embodiments, the protease is a subtilisin. In certain embodiments, the subtilisin is selected from the group consisting of: subtilisin 168, subtilisin BPN', subtilisin Carlsberg, subtilisin DY, subtilisin 147, subtilisin 309, and variants thereof.

In certain embodiments, the method further comprises recovering said protein of interest.

Aspects of the present invention include an altered Gram positive bacterial cell, wherein said altered Gram positive bacterial cell comprises at least one genetic alteration that modifies activity of one or more proteins encoded by the ykf operonas compared to a corresponding unaltered Gram positive bacterial cell grown under essentially the same culture conditions. In certain embodiments, the altered Gram positive bacterial cell is a *Bacillus* sp. strain. In certain embodiments, the *Bacillus* sp. strain is selected from the group consisting of: *B. licheniformis, B. lentus, B. subtilis, B. amyloliquefaciens, B. brevis, B. stearothermophilus, B. alkalophilus, B. coagulans, B. circulans, B. pumilus, B. lautus, B. clausii, B. megaterium*, and *B. thuringiensis*. In certain embodiments, the *Bacillus* sp. strain is a *B. subtilis* strain. In certain embodiments, the altered Gram positive bacterial cell further comprises a mutation in a gene selected from the group consisting of degU, degQ, degS, scoC4, spoIIE, and oppA. In certain embodiments, the mutation is degU(Hy)32.

In certain embodiments, the altered Gram positive bacterial cell has reduced activity of the YkfA protein as compared to the activity of the YkfA protein in a corresponding unaltered Gram positive bacterial cell grown under essentially the same culture conditions. In certain embodiments, the altered Gram positive bacterial cell has increased activity of the YkfA protein as compared to the activity of the YkfA protein in a corresponding unaltered Gram positive bacterial cell grown under essentially the same culture conditions.

In certain embodiments, the genetic alteration is in the ykfA gene of said ykf operon. In some embodiments, the genetic alteration is in the endogenous ykfA gene of the ykf operon. In certain embodiments, the ykfA gene is at least 60% identical to SEQ ID NO:1. In certain embodiments, the genetic alteration results in an alteration in an amino acid at a position corresponding to amino acid 252 or 253 of SEQ ID NO: 2. In certain embodiments, the genetic alteration results in an alteration in an amino acid at a position corresponding to amino acids 252 and 253 of SEQ ID NO: 2. In certain embodiments, the genetic alteration results in a P to L alteration in an amino acid at a position corresponding to amino acid 252 of SEQ ID NO: 2 (shown in SEQ ID NO: 4). In certain embodiments, the genetic alteration results in a V to L alteration in an amino acid at a position corresponding to amino acid 253 of SEQ ID NO: 2 (shown in SEQ ID NO: 4). In certain embodiments, genetic alterations result in a P to L alteration in an amino acid position corresponding to amino acid 252 and in a V to L alteration in an amino acid position corresponding to amino acid 253 of SEQ ID NO: 2 (shown in SEQ ID NO: 4). In certain embodiments, the altered cell expresses a protein of interest. In certain embodiments, the protein of interest is a homologous protein. In certain embodiments, the protein of interest is a heterologous protein. In certain embodiments, the protein of interest is an enzyme.

In certain embodiments, the enzyme is selected from the group consisting of: protease, cellulase, pullulanase, amylase, carbohydrase, lipase, isomerase, transferase, kinase, and phosphatase. In certain embodiments, the protein of interest is a protease. In certain embodiments, the protease is a subtilisin In certain embodiments, the subtilisin is selected from the group consisting of: subtilisin 168, subtilisin BPN', subtilisin Carlsberg, subtilisin DY, subtilisin 147, subtilisin 309, and variants thereof.

Aspects of the present invention include a method for obtaining an altered Gram positive bacterial cell with improved protein production capability comprising introducing at least one genetic alteration into a parental Gram positive bacterial cell that modifies activity of one or more proteins encoded by the ykf operon. In certain embodiments, the altered Gram positive bacterial cell is a *Bacillus* sp. strain. In certain embodiments, the *Bacillus* sp. strain is selected from the group consisting of: *B. licheniformis, B. lentus, B. subtilis, B. amyloliquefaciens, B. brevis, B. stearothermophilus, B. alkalophilus, B. coagulans, B. circulans, B. pumilus, B. lautus, B. clausii, B. megaterium*, and *B. thuringiensis*. In certain embodiments, the *Bacillus* sp. strain is a *B. subtilis* strain. In certain embodiments, the altered Gram positive bacterial cell further comprises a mutation in a gene selected from the group consisting of degU, degQ, degS, scoC4, spoIIE, and oppA. In certain embodiments, the mutation is degU(Hy)32.

In certain embodiments, the altered Gram positive bacterial cell has reduced activity of the YkfA protein as compared to the activity of the YkfA protein in a corresponding unaltered Gram positive bacterial cell grown under essentially the same culture conditions. In certain embodiments, the altered Gram positive bacterial cell has increased activity of the YkfA protein as compared to the activity of the YkfA protein in a corresponding unaltered Gram positive bacterial cell grown under essentially the same culture conditions.

In certain embodiments, the genetic alteration is in the ykfA gene of said ykf operon. In some embodiments, the genetic alteration is in the endogenous ykfA gene of the ykf operon. In certain embodiments, the ykfA gene is at least 60% identical to SEQ ID NO:1. In certain embodiments, the genetic alteration results in an alteration in an amino acid at a position corresponding to amino acid 252 or 253 of SEQ ID NO: 2. In certain embodiments, the genetic alteration results in an alteration in an amino acid at a position corresponding to amino acids 252 and 253 of SEQ ID NO: 2. In certain embodiments, the genetic alteration results in a P to L alteration in an amino acid at a position corresponding to amino acid 252 of SEQ ID NO: 2 (shown in SEQ ID NO: 4). In certain embodiments, the genetic alteration results in a V to L alteration in an amino acid at a position corresponding to amino acid 253 of SEQ ID NO: 2 (shown in SEQ ID NO: 4). In certain embodiments, genetic alterations result in a P to L alteration in an amino acid position corresponding to amino acid 252 and in a V to L alteration in an amino acid position corresponding to amino acid 253 of SEQ ID NO: 2 (shown in SEQ ID NO: 4).

In certain embodiments, the said altered Gram positive bacterial cell expresses a protein of interest. In certain embodiments, the method further comprises introducing an expression cassette encoding said protein of interest into said parental Gram positive bacterial cell. In certain embodiments, the method further comprises introducing an expression cassette encoding said protein of interest into said altered Gram positive bacterial cell. In certain embodiments, the protein of interest is a homologous protein. In certain embodiments, the protein of interest is a heterologous protein. In certain embodiments, the protein of interest is an enzyme. In certain embodiments, the enzyme is selected from the group consisting of: protease, cellulase, pullulanase, amylase, carbohydrase, lipase, isomerase, transferase, kinase, and phosphatase. In certain embodiments, the protein of interest is a protease. In certain embodiments, the protease is a subtilisin. In certain embodiments, the subtilisin is selected from the group consisting of: subtilisin 168, subtilisin BPN', subtilisin Carlsberg, subtilisin DY, subtilisin 147, subtilisin 309, and variants thereof.

In certain embodiments, the method further comprises culturing said altered Gram positive bacterial cell under conditions such that said protein of interest is expressed by said altered Gram positive bacterial cell. In certain embodiments, the method further comprises recovering said protein of interest.

Aspects of the present invention include altered Gram positive bacterial cell produced by the methods described above.

Aspects of the present invention include a polynucleotide comprising a variant sequence derived from the ykfA gene, wherein said variant sequence:
  is at least 15 nucleotides in length,
  is at least 60% identical to all or a part of SEQ ID NO:1, and
  comprises at least one genetic alteration at a nucleotide position in the ykfA gene that leads to modified activity of a YkfA protein when said at least one mutation is present in the endogenous ykfA gene of a Gram positive bacterial cell.

In certain embodiments, the genetic alteration results in an alteration in an amino acid at a position corresponding to amino acid 252 or 253 of SEQ ID NO: 2. In certain embodiments, the genetic alteration results in an alteration in an amino acid at a position corresponding to amino acid 252 and 253 of SEQ ID NO: 2. In certain embodiments, the genetic alteration results in a P to L alteration in an amino acid at a position corresponding to amino acid 252 of SEQ ID NO: 2 (shown in SEQ ID NO: 4). In certain embodiments, the genetic alteration results in a V to L alteration in an amino acid at a position corresponding to amino acid 253 of SEQ ID NO: 2 (shown in SEQ ID NO: 4). In certain embodiments, the genetic alterations result in a P to L alteration in an amino acid position corresponding to amino acid 252 and in a V to L alteration in an amino acid position corresponding to amino acid 253 of SEQ ID NO: 2 (shown in SEQ ID NO: 4). In certain embodiments, the variant sequence is at least 90% identical to all or a part of SEQ ID NO: 3. In certain embodiments, the variant sequence is identical to all or a part of SEQ ID NO: 3. In certain embodiments, the variant sequence is at least 20 nucleotides in length. In certain embodiments, the variant sequence is at least 50 nucleotides in length. In certain embodiments, the variant sequence is at least 200 nucleotides in length.

Aspects of the present invention include an isolated polypeptide comprising a variant sequence derived from the wild type YkfA polypeptide sequence (shown in SEQ ID NO: 2), wherein said variant sequence:
  is at least 5 amino acids in length,
  is at least 60% identical to all or a part of SEQ ID NO: 2, and
  comprises at least one alteration in an amino acid in the YkfA polypeptide sequence gene that leads to modified activity of a YkfA protein.

In certain embodiments, the alteration is in an amino acid at a position corresponding to amino acid 252 or 253 of SEQ ID NO: 2. In certain embodiments, the genetic alteration is in an amino acid at a position corresponding to amino acid 252 and 253 of SEQ ID NO: 2. In certain embodiments, the genetic alteration results in a P to L alteration in an amino acid at a position corresponding to amino acid 252 of SEQ ID NO: 2 (shown in SEQ ID NO: 4). In certain embodiments, the genetic alteration results in a V to L alteration in an amino acid at a position corresponding to amino acid 253 of SEQ ID NO: 2 (shown in SEQ ID NO: 4). In certain embodiments, the genetic alteration results in a P to L alteration in an amino acid position corresponding to amino acid 252 and in a V to L alteration in an amino acid position corresponding to amino acid 253 of SEQ ID NO: 2 (shown in SEQ ID NO: 4). In certain embodiments, the variant polypeptide sequence is at least 90% identical to all or a part of SEQ ID NO: 4. In certain embodiments, the variant polypeptide sequence is identical to all or a part of SEQ ID NO: 4. In certain embodiments, the variant polypeptide sequence is at least 5 amino acids in length. In certain embodiments, the variant polypeptide sequence is at least 20 amino acids in length. In certain embodiments, the variant polypeptide sequence is at least 50 amino acids in length.

Aspects of the present invention include a vector comprising the polynucleotide sequence as described above. In certain embodiments, the vector is a targeting vector designed to introduce the at least one mutation in said polynucleotide sequence into the corresponding location in the ykf operon of a Gram positive bacterial cell by homologous recombination when transformed into said Gram positive bacterial cell.

Aspects of the present invention include a method for enhancing expression of a protein of interest in a Gram positive bacterial cell comprising:
  a) transforming a parental Gram positive bacterial cell with the vector above;
  b) allowing homologous recombination of said vector and the corresponding region in the ykf operon of said parental Gram positive bacterial cell to produce an altered Gram positive bacterial cell; and
  c) growing said altered Gram positive bacterial cell under conditions suitable for the expression of said protein of interest, wherein the production of said protein of interest is increased in the altered Gram positive bacterial cell as compared to said Gram positive bacterial cell prior to said transformation in step.

In certain embodiments, the parental Gram positive bacterial cell is a *Bacillus* sp. strain. In certain embodiments, the *Bacillus* sp. strain is selected from the group consisting of: *B. licheniformis, B. lentus, B. subtilis, B. amyloliquefaciens, B. brevis, B. stearothermophilus, B. alkalophilus, B. coagulans, B. circulans, B. pumilus, B. lautus, B. clausii, B. megaterium*, and *B. thuringiensis*. In certain embodiments, the *Bacillus* sp. strain is a *B. subtilis* strain. In certain embodiments, the altered Gram positive bacterial cell further comprises a mutation in a gene selected from the group consisting of degU, degQ, degS, scoC4, spoIIE, and oppA. In certain embodiments, the mutation is degU(Hy)32.

In certain embodiments, the altered Gram positive bacterial cell has reduced activity of the YkfA protein as compared to the activity of the YkfA protein in a corresponding unaltered Gram positive bacterial cell grown under essentially the same culture conditions. In certain embodiments, the altered Gram positive bacterial cell has increased activity of the YkfA protein as compared to the activity of the YkfA protein in a corresponding unaltered Gram positive bacterial cell grown under essentially the same culture conditions.

In certain embodiments, the mutation is in the ykfA gene of said ykf operon. In some embodiments, the genetic alteration is in the endogenous ykfA gene of the ykf operon. In certain embodiments, the ykfA gene is at least 60% identical to SEQ ID NO:1. In certain embodiments, the genetic alteration results in an alteration in an amino acid at a position corresponding to amino acid 252 or 253 of SEQ ID NO: 2. In certain embodiments, the genetic alteration results in an alteration in an amino acid at a position corresponding to amino acids 252 and 253 of SEQ ID NO: 2. In certain embodiments, the genetic alteration results in a P to L alteration in an amino acid at a position corresponding to amino acid 252 of SEQ ID NO: 2 (shown in SEQ ID NO: 4). In certain embodiments, the genetic alteration results in a V to L alteration in an amino acid at a position corresponding to amino acid 253 of SEQ ID NO: 2 (shown in SEQ ID NO: 4). In certain embodiments, genetic alterations result in a P to L alteration in an amino acid position corresponding to amino acid 252 and in a V to L alteration in an amino acid position corresponding to amino acid 253 of SEQ ID NO: 2 (shown in SEQ ID NO: 4). In certain embodiments, the protein of interest is a homologous protein. In certain embodiments, the protein of interest is a heterologous protein. In certain embodiments, the protein of interest is an enzyme. In certain embodiments, the enzyme is selected from the group consisting of: protease, cellulase, pullulanase, amylase, carbohydrase, lipase, isomerase, transferase, kinase, and phosphatase. In certain embodiments, the protein of interest is a protease. In certain embodiments, the protease is a subtilisin. In certain embodiments, the subtilisin is selected from the group consisting of: subtilisin 168, subtilisin BPN', subtilisin Carlsberg, subtilisin DY, subtilisin 147, subtilisin 309, and variants thereof.

In certain embodiments, the method further comprises recovering said protein of interest.

BRIEF DESCRIPTION OF THE DRAWINGS

FIG. 2A shows a graph of cell densities of protease expressing CB15-14 derivatives: CB15-14 #1 and #2 (control strains) and CB15-14 ykfA #1 and #2 (strains containing the ykfA mutations).

DETAILED DESCRIPTION OF THE INVENTION

Figure 1:
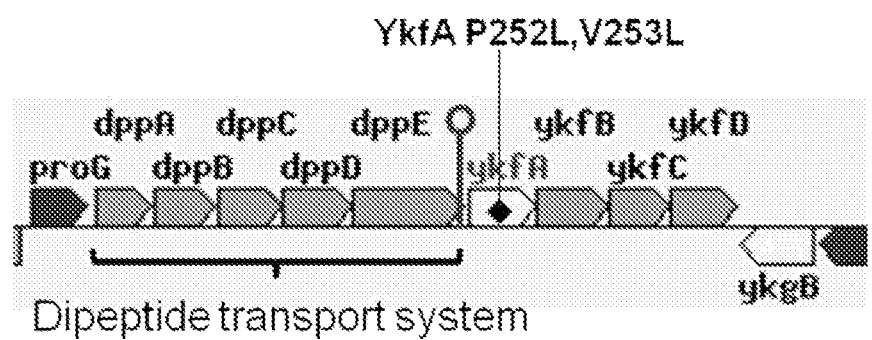
FIG. 1 shows a schematic of the ykf operon from *Bacillus subtilis*. The location of the silent mutation described in the Examples is indicated. The ykfA, ykfB, ykfC and ykfD genes are shown. Genetic alterations resulting in P252L and V253L are shown.

The present invention relates in general to bacterial cells having a genetic alteration that results in increased expression of a protein of interest and methods of making and using such cells. Aspects of the present invention include Gram-positive microorganisms, such as *Bacillus* species cells, having a genetic alteration that modifies the activity of a protein encoded by the ykf operon which results in enhanced expression of a protein of interest.

Before the present compositions and methods are described in greater detail, it is to be understood that the present compositions and methods are not limited to particular embodiments described, as such may, of course, vary. It is also to be understood that the terminology used herein is for the purpose of describing particular embodiments only, and is not intended to be limiting, since the scope of the present compositions and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present compositions and methods. The upper and lower limits of these smaller ranges may independently be included in the smaller ranges and are also encompassed within the present compositions and methods, subject to any specifically excluded limit in the stated range. Where the stated range includes one or both of the limits, ranges excluding either or both of those included limits are also included in the present compositions and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. For example, in connection with a numerical value, the term "about" refers to a range of −10% to +10% of the numerical value, unless the term is otherwise specifically defined in context. In another example, the phrase a "pH value of about 6" refers to pH values of from 5.4 to 6.6, unless the pH value is specifically defined otherwise.

The headings provided herein are not limitations of the various aspects or embodiments of the present compositions and methods which can be had by reference to the specification as a whole. Accordingly, the terms defined immediately below are more fully defined by reference to the specification as a whole.

The present document is organized into a number of sections for ease of reading; however, the reader will appreciate that statements made in one section may apply to other sections. In this manner, the headings used for different sections of the disclosure should not be construed as limiting.

Unless defined otherwise, all technical and scientific terms used herein have the same meaning as commonly understood by one of ordinary skill in the art to which the present compositions and methods belongs. Although any methods and materials similar or equivalent to those described herein can also be used in the practice or testing of the present compositions and methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present compositions and methods are not entitled to antedate such publication by virtue of prior invention. Further, the dates of publication provided may be different from the actual publication dates which may need to be independently confirmed.

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is further noted that the term "consisting essentially of," as used herein refers to a composition wherein the component(s) after the term is in the presence of other known component(s) in a total amount that is less than 30% by weight of the total composition and do not contribute to or interferes with the actions or activities of the component(s).

It is further noted that the term "comprising," as used herein, means including, but not limited to, the component(s) after the term "comprising." The component(s) after the term "comprising" are required or mandatory, but the composition comprising the component(s) may further include other non-mandatory or optional component(s).

It is also noted that the term "consisting of," as used herein, means including, and limited to, the component(s) after the term "consisting of." The component(s) after the term "consisting of" are therefore required or mandatory, and no other component(s) are present in the composition.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

DEFINITIONS

As used herein, "host cell" refers to a cell that has the capacity to act as a host or expression vehicle for a newly introduced DNA sequence.

In certain embodiments of the present invention, the host cells are bacterial cells, e.g., Gram-positive host cells *Bacillus* sp.

As used herein, "the genus *Bacillus*" or "*Bacillus* sp." includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

As used herein, "nucleic acid" refers to a nucleotide or polynucleotide sequence, and fragments or portions thereof, as well as to DNA, cDNA, and RNA of genomic or synthetic origin which may be double-stranded or single-stranded, whether representing the sense or antisense strand. It will be understood that as a result of the degeneracy of the genetic code, a multitude of nucleotide sequences may encode a given protein.

As used herein, the term "vector" refers to any nucleic acid that can be replicated in cells and can carry new genes or DNA segments into cells. Thus, the term refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. A "targeting vector" is a vector that includes polynucleotide sequences that are homologus to a regin in the choromosome of a host cell into which it is transformed and that can drive homologous recombination at that region. Targetting vectors find use in introducing mutations into the chromosome of a cell through homologous recombination. In some embodiments, the targeting vector comprises comprises other non-homologous sequences, e.g., added to the ends (i.e., stuffer sequences or flanking sequences). The ends can be closed such that the targeting vector forms a closed circle, such as, for example, insertion into a vector. Selection and/or construction of appropriate vectors is within the knowledge of those having skill in the art.

As used herein, the term "plasmid" refers to a circular double-stranded (ds) DNA construct used as a cloning vector, and which forms an extrachromosomal self-replicating genetic element in many bacteria and some eukaryotes. In some embodiments, plasmids become incorporated into the genome of the host cell.

By "purified" or "isolated" or "enriched" is meant that a biomolecule (e.g., a polypeptide or polynucleotide) is altered from its natural state by virtue of separating it from some or all of the naturally occurring constituents with which it is associated in nature. Such isolation or purification may be accomplished by art-recognized separation techniques such as ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation on a gradient to remove whole cells, cell debris, impurities, extraneous proteins, or enzymes undesired in the final composition. It is further possible to then add constituents to a purified or isolated biomolecule composition which provide additional benefits, for example, activating agents, anti-inhibition agents, desirable ions, compounds to control pH or other enzymes or chemicals.

As used herein, the terms "enhanced", "improved" and "increased" when referring to expression of a biomolecule of interest (e.g., a protein on interest) are used interchangeably herein to indicate that expression of the biomolecule is above the level of expression in a corresponding host strain (e.g., a wildtype and/or a parental strain) that has not been altered according to the teachings herein but has been grown under essentially the same growth conditions.

As used herein the term "expression" when applied to a protein refers to a process by which a protein is produced based on the nucleic acid sequence of a gene and thus includes both transcription and translation.

As used herein in the context of introducing a polynucleotide into a cell, the term "introduced" refers to any method suitable for transferring the polynucleotide into the cell. Such methods for introduction include but are not limited to protoplast fusion, transfection, transformation, conjugation, and transduction (See e.g., Ferrari et al., "*Genetics*," in Hardwood et al, (eds.), *Bacillus*, Plenum Publishing Corp., pages 57-72, [1989]).

As used herein, the terms "transformed" and "stably transformed" refers to a cell into which a polynucleotide sequence has been introduced by human intervention. The polynucleotide can be integrated into the genome of the cell or be present as an episomal plasmid that is maintained for at least two generations.

As used herein, the terms "selectable marker" or "selective marker" refer to a nucleic acid (e.g., a gene) capable of expression in host cell which allows for ease of selection of those hosts containing the nucleic acid. Examples of such selectable markers include but are not limited to antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation. Other markers useful in accordance with the invention include, but are not limited to auxotrophic markers, such as tryptophan; and detection markers, such as β-galactosidase.

As used herein, the term "promoter" refers to a nucleic acid sequence that functions to direct transcription of a downstream gene. In embodiments, the promoter is appropriate to the host cell in which the target gene is being expressed. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

As used herein, "functionally attached" or "operably linked" means that a regulatory region or functional domain having a known or desired activity, such as a promoter, terminator, signal sequence or enhancer region, is attached to or linked to a target (e.g., a gene or polypeptide) in such a manner as to allow the regulatory region or functional domain to control the expression, secretion or function of that target according to its known or desired activity.

The term "genetic alteration" or "genetic change" when used to describe a recombinant cell means that the cell has at least one genetic difference as compared to a parent cell. The one or more genetic difference may be a chromosomal mutation (e.g., an insertion, a deletion, substitution, inversion, replacement of a chromosomal region with another (e.g., replacement of a chromosomal prompter with a heterologous promoter), etc.) and/or the introduction of an extra-chromosomal polynucleotide (e.g., a plasmid). In some embodiments, an extra-chormosomal polynucleotide may be integrated into the chromosome of the host cell to generate a stable transfectant/transformant. Embodiments of the present disclosure include a genetic alterations that modify the activity of one or more proteins encoded by a gene in the ykf operon (ykfA, ykfB, ykfC, and ykfD). As detailed herein, such alterations improve the expression of a protein of interest.

As described herein, modifying activity of a protein can be achieved in any convienient manner. For example, protein activity can be modified by increasing or decreasing activity of the protein. Protein activity can also be modified by, e.g., altering protein stability, protein-protein interaction or binding, or altering substrate specificity of a protein. Modification of activity may be at the level of transcription, mRNA stability, translation, or may be due to the presence of a variation in one or more of the polypeptides produced from the ykf operon that reduces its activity (i.e., it is a "functional" reduction of expression based on activity of the polypeptide). As such, no limitation in the type of genetic alteration or the manner through which expression or activity of at least one protein encoded by the ykf operon is modified is intended. For example, in some embodiments the genetic alteration in the Gram positive cell is one that alters one or more of promoters resulting in reduced transcriptional activity. In certain embodiments, the alteration results in reduced levels of mRNA transcript. Alternatively, the genetic alteration in the Gram positive cell can be one that alters a nucleotide resulting in a transcript with reduced stability in the cell. In certain embodiments, more than one genetic alteration that reduces the expression of one or more genes may be present in the genetically altered Gram positive cell.

"Inactivation" of a gene means that the expression of a gene or the activity of its encoded biomolecule is blocked or is otherwise unable to exert its known function. Inactivation can occur via any suitable means, e.g., via a genetic alteration as described above. In one embodiment, the expression product of an inactivated gene is a truncated protein with a corresponding change in the biological activity of the protein. In some embodiments, an altered Gram positive bacterial strain comprises inactivation of one or more genes that results preferably in stable and non-reverting inactivation.

In some embodiments, inactivation is achieved by deletion. In some embodiments, the region targeted for deletion (e.g., a gene) is deleted by homologous recombination. For example, a DNA construct comprising an incoming sequence having a selective marker flanked on each side by sequences that are homologous to the region targeted for deletion is used (where the sequences may be referred to herein as a "homology box"). The DNA construct aligns with the homologous sequences of the host chromosome and in a double crossover event the region targeted for deletion is excised out of the host chromosome.

An "insertion" or "addition" is a change in a nucleotide or amino acid sequence which has resulted in the addition of one or more nucleotides or amino acid residues, respectively, as compared to the naturally occurring or parental sequence.

As used herein, a "substitution" results from the replacement of one or more nucleotides or amino acids by different nucleotides or amino acids, respectively.

Methods of mutating genes are well known in the art and include but are not limited to site-directed mutation, generation of random mutations, and gapped-duplex approaches (See e.g., U.S. Pat. No. 4,760,025; Moring et al., Biotech. 2:646 [1984]; and Kramer et al., Nucleic Acids Res., 12:9441 [1984]).

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "ortholog" and "orthologous genes" refer to genes in different species that have evolved from a common ancestral gene (i.e., a homologous gene) by speciation. Typically, orthologs retain the same function in during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity, with identity being preferred. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

As used herein, an "analogous sequence" is one wherein the function of the gene is essentially the same as the gene designated from *Bacillus subtilis* strain 168. Additionally, analogous genes include at least 60%, 65%, 70%, 75%, 80%, 85%, 90%, 95%, 97%, 98%, 99% or 100% sequence identity with the sequence of the *Bacillus subtilis* strain 168 gene. Alternately, analogous sequences have an alignment of between 70 to 100% of the genes found in the *B. subtilis* 168 region and/or have at least between 5-10 genes found in the region aligned with the genes in the *B. subtilis* 168 chromosome. In additional embodiments more than one of the above properties applies to the sequence. Analogous sequences are determined by known methods of sequence alignment. A commonly used alignment method is BLAST, although as indicated above and below, there are other methods that also find use in aligning sequences.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps.

Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). A particularly useful BLAST program is the WU-BLAST-2 program (See, Altschul et al., Meth. Enzymol., 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

As used herein, "percent (%) sequence identity" with respect to the amino acid or nucleotide sequences identified herein is defined as the percentage of amino acid residues or nucleotides in a candidate sequence that are identical with the amino acid residues or nucleotides in a MaI3A sequence, after aligning the sequences and introducing gaps, if necessary, to achieve the maximum percent sequence identity, and not considering any conservative substitutions as part of the sequence identity.

By "homologue" (or "homolog") shall mean an entity having a specified degree of identity with the subject amino acid sequences and the subject nucleotide sequences. A homologous sequence is can include an amino acid sequence that is at least 60%, 65%, 70%, 75%, 80%, 85%, 86%, 87%, 88%, 89%, 90%, 91%, 92%, 93%, 94%, 95%, 96%, 97%, 98% or even 99% identical to the subject sequence, using conventional sequence alignment tools (e.g., Clustal, BLAST, and the like). Typically, homologues will include the same active site residues as the subject amino acid sequence, unless otherwise specified.

Methods for performing sequence alignment and determining sequence identity are known to the skilled artisan, may be performed without undue experimentation, and calculations of identity values may be obtained with definiteness. See, for example, Ausubel et al., eds. (1995) *Current Protocols in Molecular Biology*, Chapter 19 (Greene Publishing and Wiley-Interscience, New York); and the ALIGN program (Dayhoff (1978) in *Atlas of Protein Sequence and Structure* 5:Suppl. 3 (National Biomedical Research Foundation, Washington, D.C.). A number of algorithms are available for aligning sequences and determining sequence identity and include, for example, the homology alignment algorithm of Needleman et al. (1970) *J. Mol. Biol.* 48:443; the local homology algorithm of Smith et al. (1981) *Adv. Appl. Math.* 2:482; the search for similarity method of Pearson et al. (1988) *Proc. Natl. Acad. Sci.* 85:2444; the Smith-Waterman algorithm (*Meth. Mol. Biol.* 70:173-187 (1997); and BLASTP, BLASTN, and BLASTX algorithms (see Altschul et al. (1990) *J. Mol. Biol.* 215:403-410).

Computerized programs using these algorithms are also available, and include, but are not limited to: ALIGN or Megalign (DNASTAR) software, or WU-BLAST-2 (Altschul et al., *Meth. Enzym.*, 266:460-480 (1996)); or GAP, BESTFIT, BLAST, FASTA, and TFASTA, available in the Genetics Computing Group (GCG) package, Version 8, Madison, Wis., USA; and CLUSTAL in the PC/Gene program by Intelligenetics, Mountain View, Calif. Those skilled in the art can determine appropriate parameters for measuring alignment, including algorithms needed to achieve maximal alignment over the length of the sequences being compared. Preferably, the sequence identity is determined using the default parameters determined by the program. Specifically, sequence identity can determined by using Clustal W (Thompson J. D. et al. (1994) Nucleic Acids Res. 22:4673-4680) with default parameters, i.e.:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF As used herein, the term "hybridization" refers to the process by which a strand of nucleic acid joins with a complementary strand through base pairing, as known in the art.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while an intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5× SSC, 5× Denhardt's solution, 0.5% SDS and 100 μg/ml denatured carrier DNA followed by washing two times in 2× SSC and 0.5% SDS at room temperature and two additional times in 0.1× SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

The term "recombinant," when used in reference to a biological component or composition (e.g., a cell, nucleic acid, polypeptide/enzyme, vector, etc.) indicates that the biological component or composition is in a state that is not found in nature. In other words, the biological component or composition has been modified by human intervention from its natural state. For example, a recombinant cell encompass a cell that expresses one or more genes that are not found in its native parent (i.e., non-recombinant) cell, a cell that expresses one or more native genes in an amount that is different than its native parent cell, and/or a cell that expresses one or more native genes under different conditions than its native parent cell. Recombinant nucleic acids may differ from a native sequence by one or more nucleotides, be operably linked to heterologous sequences (e.g., a heterologous promoter, a sequence encoding a non-native or variant signal sequence, etc.), be devoid of intronic sequences, and/or be in an isolated form. Recombinant polypeptides/enzymes may differ from a native sequence by one or more amino acids, may be fused with heterologous sequences, may be truncated or have internal deletions of amino acids, may be expressed in a manner not found in a native cell (e.g., from a recombinant cell that over-expresses the polypeptide due to the presence in the cell of an expression vector encoding the polypeptide), and/or be in an isolated form. It is emphasized that in some embodiments, a recombinant polynucleotide or polypeptide/enzyme has a sequence that is identical to its wild-type counterpart but is in a non-native form (e.g., in an isolated or enriched form).

As used herein, the term "target sequence" refers to a DNA sequence in the host cell that encodes the sequence where it is desired for the incoming sequence to be inserted into the host cell genome. In some embodiments, the target sequence encodes a functional wild-type gene or operon, while in other embodiments the target sequence encodes a functional mutant gene or operon, or a non-functional gene or operon.

As used herein, a "flanking sequence" refers to any sequence that is either upstream or downstream of the sequence being discussed (e.g., for genes A-B-C, gene B is flanked by the A and C gene sequences). In a embodiment, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in embodiments, it is on each side of the sequence being flanked. The sequence of each homology box is homologous to a sequence in the *Bacillus* chromosome. These sequences direct where in the *Bacillus* chromosome the new construct gets integrated and what part of the *Bacillus* chromosome will be replaced by the incoming sequence. In a embodiment, the 5' and 3' ends of a selective marker are flanked by a polynucleotide sequence comprising a section of the inactivating chromosomal segment. In some embodiments, a flanking sequence is present on only a single side (either 3' or 5'), while in embodiments, it is present on each side of the sequence being flanked.

As used herein, the terms "amplifiable marker," "amplifiable gene," and "amplification vector" refer to a gene or a vector encoding a gene which permits the amplification of that gene under appropriate growth conditions.

"Template specificity" is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (See e.g., Kacian et al., Proc. Natl. Acad. Sci. USA 69:3038 [1972]). Other nucleic acids are not replicated by this amplification enzyme. Similarly, in the case of T7 RNA polymerase, this amplification enzyme has a stringent specificity for its own promoters (See, Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (See, Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "amplifiable nucleic acid" refers to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, "genetically altered host strain" (e.g., a genetically altered *Bacillus* strain) refers to a genetically engineered host cell, also called a recombinant host cell. In some embodiments, the genetically altered host cell has enhanced (increased) expression of a protein of interest as compared to the expression and/or production of the same protein of interest in a corresponding unaltered host strain grown under essentially the same growth conditions. In some embodiments, the enhanced level of expression results from modified activity of one or more proteins encoded by the ykf operon. In some embodiments, the altered strains are genetically engineered *Bacillus* sp. having one or more deleted indigenous chromosomal regions or fragments thereof, wherein a protein of interest has an enhanced level of expression or production, as compared to a corresponding unaltered *Bacillus* host strain grown under essentially the same growth conditions.

As used herein, a "corresponding unaltered *Bacillus* strain" and the like is the host strain (e.g., the originating (parental) and/or wild-type strain) which does not have the indicated genetic alteration.

As used herein, the term "chromosomal integration" refers to the process whereby the incoming sequence is introduced into the chromosome of a host cell (e.g., *Bacillus*). The homologous regions of the transforming DNA align with homologous regions of the chromosome. Subsequently, the sequence between the homology boxes is replaced by the incoming sequence in a double crossover (i.e., homologous recombination). In some embodiments of the present invention, homologous sections of an inactivating chromosomal segment of a DNA construct align with the flanking homologous regions of the indigenous chromosomal region of the *Bacillus* chromosome. Subsequently, the indigenous chromosomal region is deleted by the DNA construct in a double crossover (i.e., homologous recombination).

"Homologous recombination" means the exchange of DNA fragments between two DNA molecules or paired chromosomes at the site of identical or nearly identical nucleotide sequences. In a embodiment, chromosomal integration is homologous recombination.

"Homologous sequences" as used herein means a nucleic acid or polypeptide sequence having 100%, 99%, 98%, 97%, 96%, 95%, 94%, 93%, 92%, 91%, 90%, 88%, 85%, 80%, 75%, or 70% sequence identity to another nucleic acid or polypeptide sequence when optimally aligned for comparison. In some embodiments, homologous sequences have between 85% and 100% sequence identity, while in other embodiments there is between 90% and 100% sequence identity, and in more embodiments, there is 95% and 100% sequence identity.

As used herein "amino acid" refers to peptide or protein sequences or portions thereof. The terms "protein", "peptide" and "polypeptide" are used interchangeably.

As used herein, "protein of interest" and "polypeptide of interest" refer to a protein/polypeptide that is desired and/or being assessed. In some embodiments, the protein of interest is intracellular, while in other embodiments, it is a secreted polypeptide. Particularly polypeptides include enzymes, including, but not limited to those selected from amylolytic enzymes, proteolytic enzymes, cellulytic enzymes, oxidoreductase enzymes and plant cell-wall degrading enzymes. More particularly, these enzyme include, but are not limited to amylases, proteases, xylanases, lipases, laccases, phenol oxidases, oxidases, cutinases, cellulases, hemicellulases, esterases, perioxidases, catalases, glucose oxidases, phytases, pectinases, glucosidases, isomerases, transferases, galactosidases and chitinases. In particular embodiments of the present invention, the polypeptide of interest is a protease. In some embodiments, the protein of interest is a secreted polypeptide which is fused to a signal peptide (i.e., an amino-terminal extension on a protein to be secreted). Nearly all secreted proteins use an amino-terminal protein extension which plays a crucial role in the targeting to and translocation of precursor proteins across the membrane. This extension is proteolytically removed by a signal peptidase during or immediately following membrane transfer.

In some embodiments of the present invention, the polypeptide of interest is selected from hormones, antibodies, growth factors, receptors, etc. Hormones encompassed by the present invention include but are not limited to, follicle-stimulating hormone, luteinizing hormone, corticotropin-releasing factor, somatostatin, gonadotropin hormone, vasopressin, oxytocin, erythropoietin, insulin and the like. Growth factors include, but are not limited to platelet-derived growth factor, insulin-like growth factors, epidermal growth factor, nerve growth factor, fibroblast growth factor, transforming growth factors, cytokines, such as interleukins (e.g., IL-1 through IL-13), interferons, colony stimulating factors, and the like. Antibodies include but are not limited to immunoglobulins obtained directly from any species from which it is desirable to produce antibodies. In addition, the present invention encompasses modified antibodies. Polyclonal and monoclonal antibodies are also encompassed by the present invention. In particularly embodiments, the antibodies are human antibodies.

As used herein, a "derivative" or "variant" of a polypeptide means a polypeptide, which is derived from a precursor polypeptide (e.g., the native polypeptide) by addition of one or more amino acids to either or both the C- and N-terminal ends, substitution of one or more amino acids at one or a number of different sites in the amino acid sequence, deletion of one or more amino acids at either or both ends of the polypeptide or at one or more sites in the amino acid sequence, insertion of one or more amino acids at one or more sites in the amino acid sequence, and any combination thereof. The preparation of a derivative or variant of a polypeptide may be achieved in any convenient manner, e.g., by modifying a DNA sequence which encodes the native polypeptides, transformation of that DNA sequence into a suitable host, and expression of the modified DNA sequence to form the derivative/variant polypeptide. Derivatives or variants further include polypeptides that are chemically modified.

As used herein, the term "heterologous protein" refers to a protein or polypeptide that does not naturally occur in the host cell. Examples of heterologous proteins include enzymes such as hydrolases including proteases, cellulases, amylases, carbohydrases, and lipases; isomerases such as racemases, epimerases, tautomerases, or mutases; transferases, kinases and phophatases. In some embodiments, the proteins are therapeutically significant proteins or peptides, including but not limited to growth factors, cytokines, ligands, receptors and inhibitors, as well as vaccines and antibodies. In additional embodiments, the proteins are commercially important industrial proteins/peptides (e.g., proteases, carbohydrases such as amylases and glucoamylases, cellulases, oxidases and lipases). In some embodiments, the gene encoding the proteins are naturally occurring genes, while in other embodiments, mutated and/or synthetic genes are used.

As used herein, "homologous protein" refers to a protein or polypeptide native or naturally occurring in a cell. In embodiments, the cell is a Gram-positive cell, while in particularly embodiments, the cell is a *Bacillus* host cell. In alternative embodiments, the homologous protein is a native protein produced by other organisms, including but not limited to *E. coli*. The invention encompasses host cells producing the homologous protein via recombinant DNA technology.

As used herein, an "operon" comprises a group of contiguous genes that can be transcribed as a single transcription unit from a common promoter, and are thereby subject to co-regulation. In some embodiments, an operon may include multiple promoters that drive the transcription of multiple different mRNAs.

The present invention relates in general to bacterial cells having a genetic alteration that results in increased expression of a protein of interest and methods of making and using such cells. Aspects of the present invention include Gram-positive microorganisms, such as *Bacillus* species, having a genetic alteration that modifies activity of a protein encoded by the ykf operon and results in enhanced expression of a protein of interest.

As summarized above, aspects of the invention include methods for increasing expression of a protein of interest from a Gram positive bacterial cell and is based on the observation that the production of a protein of interest is increased in Gram positive cells that have been genetically altered to have modified activity of one or more proteins encoded by the ykf operon (e.g., ykfA) is as compared to the expression level of the same protein of interest in a corresponding non-genetically altered Gram positive cell (e.g., a wild type and/or a parental cell). In some embodiments, the Gram positive cells have been genetically altered to have reduced activity of one or more proteins encoded by the ykf operon (e.g., ykfA). In some embodiments, the Gram positive cells have been genetically altered to have increased activity of one or more proteins encoded by the ykf operon (e.g., ykfA). By genetic alteration is meant any alteration in a host cell that changes the genetic make-up of the host cell, for example by episomal addition and/or chromosomal insertion, deletion, inversion, base change, etc. No limitation in this regard is intended.

In certain embodiments, the method involves producing or obtaining an altered Gram positive bacterial cell that comprises at least one genetic alteration that modifies activity of one or more proteins encoded by the ykf operon and that is capable of producing a protein of interest and culturing the altered Gram positive bacterial cell under conditions such that the protein of interest is expressed by the altered Gram positive bacterial cell. Expression of the protein of interest is thereby increased in the altered Gram positive bacterial cell compared to the expression of the protein of interest in a corresponding unaltered Gram positive bacterial cell grown under essentially the same culture conditions.

According to certain embodiments, the genetically altered Gram positive bacterial cell (or parental cell from which the genetically altered Gram positive bacterial cell is produced) can be a *Bacillus* strain. In some embodiments, the *Bacillus* strain of interest is alkalophilic. Numerous alkalophilic *Bacillus* strains are known (See e.g., U.S. Pat. No. 5,217,878; and Aunstrup et al., Proc IV IFS: Ferment. Technol. Today, 299-305 [1972]). In some embodiments, the *Bacillus* strain of interest is an industrial *Bacillus* strain. Examples of industrial *Bacillus* strains include, but are not limited to *B. licheniformis*, *B. lentus*, *B. subtilis*, and *B. amyloliquefaciens*. In additional embodiments, the *Bacillus* host strain is selected from the group consisting of *B. lentus*, *B. brevis*, *B. stearothermophilus*, *B. alkalophilus*, *B. coagulans*, *B. circulans*, *B. pumilus*, *B. thuringiensis*, *B. clausii*, and *B. megaterium*, as well as other organisms within the genus *Bacillus*, as discussed above. In particular embodiments, *B. subtilis* is used. For example, U.S. Pat. Nos. 5,264,366 and 4,760,025 (RE 34,606) describe various *Bacillus* host strains that find use in the present invention, although other suitable strains are contemplated for use in the present invention.

The parental strain of a genetically altered cell as described herein (e.g., a parental *Bacillus* strain) may be an industrial strain, which includes non-recombinant strains, mutant strains of a naturally occurring strain, or a recombinant strain. In certain embodiments, the parental strain is a recombinant host strain wherein a polynucleotide encoding a polypeptide of interest has been introduced into the host. While the introduction of a polynucleotide encoding a polypeptide of interest may be done in a parental strain, this step may also be performed in a strain that has already been genetically altered for increased polypeptide production as detailed herein. In some embodiments, the host strain is a *Bacillus subtilis* host strain, e.g., a recombinant *B. subtilis* host strain.

Numerous *B. subtilis* strains are known that find use in aspects of the present invention, including but not limited to 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain (See e.g., Hoch et al., Genetics, 73:215-228 [1973]; U.S. Pat. Nos. 4,450,235; 4,302,544; and EP 0134048). The use of *B. subtilis* as an expression host is further described by Palva et al. and others (See, Palva et al., Gene 19:81-87 [1982]; also see Fahnestock and Fischer, J. Bacteriol., 165:796-804 [1986]; and Wang et al., Gene 69:39-47 [1988]).

In certain embodiments, industrial protease producing *Bacillus* strains can serve as parental expression hosts. In some embodiments, use of these strains in the present invention provides further enhancements in efficiency and protease production. Two general types of proteases are typically secreted by *Bacillus* sp., namely neutral (or "metalloproteases") and alkaline (or "serine") proteases. Serine proteases are enzymes which catalyze the hydrolysis of peptide bonds in which there is an essential serine residue at the active site. Serine proteases have molecular weights in the 25,000 to 30,000 range (See, Priest, Bacteriol. Rev., 41:711-753 [1977]). Subtilisin is a serine protease for use in the present invention. A wide variety of *Bacillus* subtilisins have been identified and sequenced, for example, subtilisin 168, subtilisin BPN', subtilisin Carlsberg, subtilisin DY, subtilisin 147 and subtilisin 309 (See e.g., EP 414279 B; WO 89/06279; and Stahl et al., J. Bacteriol., 159:811-818 [1984]). In some embodiments of the present invention, the *Bacillus* host strains produce mutant (e.g., variant) proteases. Numerous references provide examples of variant proteases and reference (See e.g., WO 99/20770; WO 99/20726; WO 99/20769; WO 89/06279; RE 34,606; U.S. Pat. Nos. 4,914,031; 4,980,288; 5,208,158; 5,310,675; 5,336,611; 5,399,283; 5,441,882; 5,482,849; 5,631,217; 5,665,587; 5,700,676; 5,741,694; 5,858,757; 5,880,080 6,197,567; and U.S. Pat. No. 6,218,165).

It is noted here that the present invention is not limited to proteases as the protein of interest. Indeed, the present disclosure encompasses a wide variety of proteins of interest for which increased expression in the Gram positive cell is desired (detailed below).

In other embodiments, a strain for use in aspects of the present invention may have additional genetic alterations in other genes that provide beneficial phenotypes. For example, a *Bacillus* sp. that includes a mutation or deletion in at least one of the following genes, degU, degS, degR and degQ may be employed. In some embodiments, the mutation is in a degU gene, e.g., a degU(Hy)32 mutation. (See, Msadek et al., J. Bacteriol., 172:824-834 [1990]; and Olmos et al., Mol. Gen. Genet., 253:562-567 [1997]). Thus, one example of a parental/genetically altered Gram positive strain that finds use in aspects of the present invention is a *Bacillus subtilis* cell carrying a degU32(Hy) mutation. In a further embodiment, the *Bacillus* host may include a mutation or deletion in scoC4, (See, Caldwell et al., J. Bacteriol., 183:7329-7340 [2001]); spoIIE (See, Arigoni et al., Mol. Microbiol., 31:1407-1415 [1999]); oppA or other genes of the opp operon (See, Perego et al., Mol. Microbiol., 5:173-185 [1991]). Indeed, it is contemplated that any mutation in the opp operon that causes the same phenotype as a mutation in the oppA gene will find use in some embodiments of the altered *Bacillus* strain of the present invention. In some embodiments, these mutations occur alone, while in other embodiments, combinations of mutations are present. In some embodiments, an altered *Bacillus* of the invention is obtained from a parental *Bacillus* host strain that already includes a mutation to one or more of the above-mentioned genes. In alternate embodiments, a previously genetically altered *Bacillus* of the invention is further engineered to include mutation of one or more of the above-mentioned genes.

In certain embodiments, the activity of the one or more proteins encoded by the ykf operon is reduced in the genetically altered Gram positive cell to about 3% of the level of activity in the wildtype and/or parental cell cultured under essentially the same culture conditions, including about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 65%, about 70%, about 75%, or about 80%. As such, the range of reduction of expression of the one or more genes in the ykf operon can be from about 3% to about 80%, from about 4% to about 75%, from about 5% to about 70%, from about 6% to about 65%, from about 7% to about 60%, from about 8% to about 50%, from about 9% to about 45%, from about 10% to about 40%, from about 11% to about 35%, from about 12% to about 30%, from about 13% to about 25%, from about 14% to about 20%, etc. Any sub-range of expression within the ranges set forth above is contemplated.

In certain embodiments, the activity of the one or more proteins encoded by the ykf operon is increased in the genetically altered Gram positive cell to about 3% of the level of activity in the wildtype and/or parental cell cultured under essentially the same culture conditions, including about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 65%, about 70%, about 75%, or about 80%. As such, the range of reduction of expression of the one or more genes in the ykf operon can be from about 3% to about 80%, from about 4% to about 75%, from about 5% to about 70%, from about 6% to about 65%, from about 7% to about 60%, from about 8% to about 50%, from about 9% to about 45%, from about 10% to about 40%, from about 11% to about 35%, from about 12% to about 30%, from about 13% to about 25%, from about 14% to about 20%, etc. Any sub-range of expression within the ranges set forth above is contemplated.

In certain embodiments, the altered Gram positive bacterial cell has modified activity of the YkfA protein, and/or the YkfB protein, and/or the YkfC protein, and/or the YkfD protein, or any combination thereof, as compared to the activity of these proteins in a corresponding unaltered Gram positive bacterial cell grown under essentially the same culture conditions.

In one embodiment, the gene that is mutated belongs to the peptidase S66 super-family. In certain embodiments, the gene that is mutated is a carboxypeptidase belonging to the peptidase S66 super-family. In certain embodiments, the carboxypeptidase that is mutated is at least 60% homologous to a gene encoded by the ykf operon. In certain embodiments, the carboxypeptidase that is mutated is at least 60% homologous to a gene encoded by ykfA (shown in SEQ ID NO: 1).

In certain embodiments, the genetic alteration is in the ykfA gene of the ykf operon. A ykfA gene in a parental Gram positive cell (i.e., prior to being genetically altered as described herein) is a gene that is at least 60% identical to SEQ ID NO:1, including at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or 100% identical to SEQ ID NO:1. In certain embodiments, the genetic alteration results in an alteration in an amino acid at a position corresponding to amino acid 252 or 253 of SEQ ID NO: 2. In certain embodiments, the genetic alteration results in an alteration in an amino acid at a position corresponding to amino acids 252 and 253 of SEQ ID NO: 2. In certain embodiments, the genetic alteration results in a P to L alteration in an amino acid at a position corresponding to amino acid 252 of SEQ ID NO: 2 (as shown in SEQ ID NO: 4). In certain embodiments, the genetic alteration results in a V to L alteration in an amino acid at a position corresponding to amino acid 253 of SEQ ID NO: 2 (as shown in SEQ ID NO: 4). In certain embodiments, the genetic alteration results in a P to L alteration in an amino acid position corresponding to amino acid 252 and in a V to L alteration in an amino acid position corresponding to amino acid 253 of SEQ ID NO: 2 (as shown in SEQ ID NO: 4).

As indicated above, many different proteins find use as the protein of interest in the Gram positive cell (i.e., the protein whose expression is increased in the genetically altered cell). The protein of interest can be a homologous protein or a heterologous protein and may be a wildtype protein or a natural or recombinant variant. In certain embodiments, the protein of interest is an enzyme, where in certain instances, the enzyme is selected from a protease, cellulase, pullulanase, amylase, carbohydrase, lipase, isomerase, transferase, kinase, and phosphatase. In certain embodiments, the protein of interest is a protease, where the protese may be a subtilisin, e.g., a subtilisin selected from subtilisin 168, subtilisin BPN', subtilisin Carlsberg, subtilisin DY, subtilisin 147, subtilisin 309, and variants thereof. In certain embodiments, the protein of interest is a fluorescent protein, e.g., green fluorescent protein (GFP).

In certain embodiments, the method further comprises recovering the protein of interest. Because the level of expression/production of the protein of interest is increased in the genetically altered Gram positive cell (as compared to q wildtype or parental cell), the amount of the protein of interest recovered is increases as compared to the corresponding wildtype and/or parental cell cultured under essential the same culture conditions (and at the same scale). There are various assays known to those of ordinary skill in the art for detecting and measuring the expression level/production of intracellularly and extracellularly expressed polypeptides. Such assays will be determined by the user of the present invention and may depend on the identity and/or activity (e.g., enzymatic activity) of the protein of interest. For example, for proteases, there are assays based on the release of acid-soluble peptides from casein or hemoglobin measured as absorbance at 280 nm or colorimetrically using the Folin method (See e.g., Bergmeyer et al., "Methods of Enzymatic Analysis" vol. 5, *Peptidases, Proteinases and their Inhibitors*, Verlag Chemie, Weinheim [1984]). Other assays involve the solubilization of chromogenic substrates (See e.g., Ward, "Proteinases," in Fogarty (ed.)., *Microbial Enzymes and Biotechnology*, Applied Science, London, [1983], pp 251-317). Other examples of assays include succinyl-Ala-Ala-Pro-Phe-para nitroanilide assay (SAAP-FpNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et a)., Anal. Biochem., 223:119-129 [1994]; and Hsia et al., Anal Biochem., 242:221-227 [1999]).

Also as indicated above, means for determining the levels of secretion of a protein of interest in a host cell and detecting expressed proteins include the use of immunoassays with either polyclonal or monoclonal antibodies specific for the protein of interest. Examples include enzyme-linked immunosorbent assay (ELISA), radioimmunoassay (RIA), fluorescence immunoassay (FIA), and fluorescent activated cell sorting (FACS). However, other methods are known to those in the art and find use in assessing the protein of interest (See e.g., Hampton et al., *Serological Methods, A Laboratory Manual*, APS Press, St. Paul, Minn. [1990]; and Maddox et al., J. Exp. Med., 158:1211 [1983]). As known in the art, the altered *Bacillus* cells produced using the present invention are maintained and grown under conditions suitable for the expression and recovery of a polypeptide of interest from cell culture (See e.g., Hardwood and Cutting (eds.) *Molecular Biological Methods for Bacillus*, John Wiley & Sons [1990]). It is further noted that a genetically altered cell as described herein may express more than one protein of interest, including two or more, three or more, four or more, five or more, six or more, seven or more, eight or more, nine or more, ten or more, etc. In some embodiments, increased expression of proteins in the bacterial secretome is desired, which includes numerous different proteins that are secreted from the cell.

Aspects of the present invention include a method for obtaining an altered Gram positive bacterial cell with improved protein production capability. In general, the method includes genetically altering a parental Gram positive cell to result in a genetically altered strain in which the activity one or more proteins encoded by the ykf operon is modified (as defined above).

In certain embodiments, the method includes introducing a polynucleotide sequence into a parental Gram positive bacterial cell that, when integrated into the chromosome or sustained as an episomal genetic element, results in a genetically altered Gram positive cell in which the activity of one or more proteins encoded by the ykf operon is modified.

Various methods are known for the transformation of *Bacillus* species to alter the chromosome of, or to maintain an episomal genetic element in, *Bacillus* using polynucleodotide vectors (e.g., plasmid constructs) are well known. Suitable methods for introducing polynucleotide sequences into *Bacillus* cells are found in, e.g., Ferrari et al., "Genetics," in Harwood et al. (ed.), *Bacillus*, Plenum Publishing Corp. [1989], pages 57-72; See also, Saunders et al., J. Bacteriol., 157:718-726 [1984]; Hoch et al., J. Bacteriol., 93:1925-1937 [1967]; Mann et al., Current Microbiol., 13:131-135 [1986]; and Holubova, Folia Microbiol., 30:97 [1985]; for *B. subtilis*, Chang et al., Mol. Gen. Genet., 168:11-115 [1979]; for *B. megaterium*, Vorobjeva et al., FEMS Microbiol. Lett., 7:261-263 [1980]; for *B amyloliquefaciens*, Smith et al., Appl. Env. Microbiol., 51:634 (1986); for *B. thuringiensis*, Fisher et al., Arch. Microbiol., 139:213-217 [1981]; and for *B. sphaericus*, McDonald, J. Gen. Microbiol., 130:203 [1984]. Indeed, such methods as transformation including protoplast transformation and congression, transduction, and protoplast fusion are known and suited for use in the present invention. Methods of transformation are particularly to introduce a DNA construct provided by the present invention into a host cell In addition, introduction of a DNA construct into the host cell includes physical and chemical methods known in the art to introduce DNA into a host cell without insertion of the targeting DNA construct into a plasmid or vector. Such methods include, but are not limited to calcium chloride precipitation, electroporation, naked DNA, liposomes and the like. In additional embodiments, DNA constructs can be co-transformed with a plasmid, without being inserted into the plasmid.

In embodiments in which selectable marker genes are used to select for stable transformants, it may be desireable to delete the selective marker from the genetically altered Gram positive strain using any convenient method, with numerous methods being known in the art (See, Stahl et al., J. Bacteriol., 158:411-418 [1984]; and Palmeros et al., Gene 247:255-264 [2000]).

In some embodiments, two or more DNA constructs (i.e., DNA constructs that each are designed to genetically alter a host cell) are introduced into a parental Gram positive cell, resulting in the introduction of two or more genetic alterations in the cell, e.g., alterations at two or more chromosomal regions. In some embodiments, these regions are contiguous, (e.g., two regions within the ykf operon or within the ykf operon and an adjacent gene or operon), while in other embodiments, the regions are separated. In some embodiments, one or more of the genetic alterations are by addition of an episomal genetic element.

In some embodiments, host cells are transformed with one or more DNA constructs according to the present invention to produce an altered *Bacillus* strain wherein two or more genes have been inactivated in the host cell. In some embodiments, two or more genes are deleted from the host cell chromosome. In alternative embodiments, two or more genes are inactivated by insertion of a DNA construct. In some embodiments, the inactivated genes are contiguous (whether inactivated by deletion and/or insertion), while in other embodiments, they are not contiguous genes.

Once a genetically altered host cell is produced, it can be cultured under conditions such that the protein of interest is expressed, where in certain embodiments the protein of interest is recovered.

Aspects of the present invention include an altered Gram positive bacterial cell, wherein the altered Gram positive bacterial cell comprises at least one genetic alteration that modifies activity of one or more proteins encoded by the ykf operon as compared to a corresponding unaltered Gram positive bacterial cell grown under essentially the same culture conditions. In some embodiments, the genetically altered Gram positive cell is produced as described above. As further noted above, the altered Gram positive bacterial cell can be a Bacillus sp. strain, e.g., a B. licheniformis, B. lentus, B. subtilis, B. amyloliquefaciens, B. brevis, B. stearothermophilus, B. alkalophilus, B. coagulans, B. circulans, B. pumilus, B. lautus, B. clausii, B. megaterium, or B. thuringiensis strain. In certain embodiments, the Bacillus sp. strain is a B. subtilis strain. In some aspects, the altered Gram positive bacterial cell further comprises an additional mutation that improves a phenotype of the cell, e.g., a mutation in a gene selected from the group consisting of degU, degQ, degS, scoC4, spoIIE, and oppA. In certain embodiments, the mutation is degU(Hy)32.

In some embodiments, the present invention includes a DNA construct comprising an incoming sequence that, when stably incorporated into the host cell, genetically alters the cell such that activity of one or more proteins encoded by the ykf operon is modified (as described in detail above). In some embodiments, the DNA construct is assembled in-vitro, followed by direct cloning of the construct into a competent Gram positive (e.g., Bacillus) host such that the DNA construct becomes integrated into the host cell chromosome. For example, PCR fusion and/or ligation can be employed to assemble a DNA construct in vitro. In some embodiments, the DNA construct is a non-plasmid construct, while in other embodiments it is incorporated into a vector (e.g., a plasmid). In some embodiments, circular plasmids are used. In embodiments, circular plasmids are designed to use an appropriate restriction enzyme (i.e., one that does not disrupt the DNA construct). Thus, linear plasmids find use in the present invention. However, other methods are suitable for use in the present invention, as known to those in the art (See e.g., Perego, "Integrational Vectors for Genetic Manipulation in Bacillus subtilis," in (Sonenshein et al. (eds.), Bacillus subtilis and Other Gram-Positive Bacteria, American Society for Microbiology, Washington, D.C. [1993]).

In certain embodiments, the incoming sequence of a DNA targeting vector includes a polynucleotide comprising a variant sequence derived from the ykfA gene. In some of these embodiments, the variant sequence is at least about 15 nucleotides in length, is at least 60% identical to all or a part of SEQ ID NO: 1, and has at least one mutation at a nucleotide position in the ykfA gene that leads to modified activity of a protein encoded by the ykf operon when the mutation is present in the endogenous ykfA gene of a Gram positive bacterial cell. The variant sequence can be at least about 20 nucleotides, about 30 nucleotides, about 40 nucleotides, about 50 nucleotides, about 60 nucleotides, about 80 nucleotides, about 90 nucleotides, about 100 nucleotides, about 200 nucleotides, about 300 nucleotides, about 400 nucleotides, about 500 nucleotides, about 600 nucleotides, about 700 nucleotides, about 800 nucleotides, about 900 nucleotides, about 1000 nucleotides, about 1100 nucleotides, about 1200 nucleotides, about 1300 nucleotides, about 1400 or more nucleotides. As further noted above, the variant sequence can be at least 60% identical to SEQ ID NO:1, including at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to SEQ ID NO:1. In certain embodiments, the genetic alteration results in an alteration in an amino acid at a position corresponding to amino acid 252 or 253 of SEQ ID NO: 2. In certain embodiments, the genetic alteration results in an alteration in an amino acid at a position corresponding to amino acids 252 and 253 of SEQ ID NO: 2. In certain embodiments, the genetic alteration results in a P to L alteration in an amino acid at a position corresponding to amino acid 252 of SEQ ID NO: 2 (as shown in SEQ ID NO: 4). In certain embodiments, the genetic alteration results in a V to L alteration in an amino acid at a position corresponding to amino acid 253 of SEQ ID NO: 2 (as shown in SEQ ID NO: 4). In certain embodiments, the genetic alteration results in a P to L alteration in an amino acid position corresponding to amino acid 252 and in a V to L alteration in an amino acid position corresponding to amino acid 253 of SEQ ID NO: 2 (as shown in SEQ ID NO: 4).

Aspects of the present invention include a vector comprising the polynucleotide sequence as described above. In certain embodiments, the vector is a targeting vector designed to introduce the at least one mutation in the polynucleotide sequence into the corresponding location in the ykf operon of a Gram positive bacterial cell by homologous recombination when transformed into the Gram positive bacterial cell. In some embodiments, the incoming sequence/vector includes a selective marker. In some embodiment, the selective marker located between two loxP sites (See, Kuhn and Torres, Meth. Mol. Biol., 180:175-204 [2002]), and the antimicrobial gene is then deleted by the action of Cre protein.

Aspects of the present invention include a method for enhancing expression of a protein of interest in a Gram positive bacterial cell that includes transforming a parental Gram positive bacterial cell with the DNA construct or vector described above (i.e., one that includes an incoming sequence that, when stably incorporated into the host cell, genetically alters the cell such that activity of one or more proteins encoded by the ykf operon is modified, e.g., one that includes a mutation in the ykfA gene as set forth above), allowing homologous recombination of the vector and the corresponding region in the ykf operon of the parental Gram positive bacterial cell to produce an altered Gram positive bacterial cell; and growing the altered Gram positive bacterial cell under conditions suitable for the expression of the protein of interest, where the production of the protein of interest is increased in the altered Gram positive bacterial cell as compared to the Gram positive bacterial cell prior to the transformation in step. Examples of the Gram positive strains, mutations and other features that find use in this aspect of the invention are described in detail above.

Whether the DNA construct is incorporated into a vector or used without the presence of plasmid DNA, it is used to transform microorganisms. It is contemplated that any suitable method for transformation will find use with the present invention. In embodiments, at least one copy of the DNA construct is integrated into the host Bacillus chromosome. In some embodiments, one or more DNA constructs of the invention are used to transform host cells.

The manner and method of carrying out the present invention may be more fully understood by those of skill in the art by reference to the following examples, which examples are not intended in any manner to limit the scope of the present invention or of the claims directed thereto.
EXPERIMENTAL The following Examples are provided in order to demonstrate and further illustrate certain embodiments and aspects of the present invention and are not to be construed as limiting the scope thereof.

In the experimental disclosure which follows, certain of the following abbreviations apply: ° C. (degrees Centigrade); rpm (revolutions per minute); µg (micrograms); mg (milligrams); µl (microliters); ml (milliliters); mM (millimolar); µM (micromolar); sec (seconds); min(s) (minute/minutes); hr(s) (hour/hours); $OD_{280}$ (optical density at 280 nm); $OD_{600}$ (optical density at 600 nm); PCR (polymerase chain reaction); RT-PCR (reverse transcription PCR); SDS (sodium dodecyl sulfate).

Example 1

Effect of Mutations in the ykfA Gene on Protein Expression in *Bacillus* Species The ykfA gene of *Bacillus subtilis* is the first coding sequence of the ykf operon (FIG. 1) that is involved in the recycling of the peptidoglycan. YfkA is a LD-carboxypeptidase that cleaves amide bonds between L- and D-amino acids, which occur naturally in bacterial peptidoglycan.

Three single nucleotide polymorphisms have been identified that result in two non-synonymous mutations (P252L and V253L) in the ykfA gene of a *Bacillus* strain. The method described by Janes and Stibitz (Infection and Immunity, 74(3):1949, 2006) was used to introduce the ykfA mutations in a suitable *Bacillus* strain, CB15-14, (amyE::xylRPxylAcomK-ermC, ΔoppA, ΔspoIIE, ΔaprE, ΔnprE, degUHy32, ΔscoC).

To test the effect of the ykfA mutations on expression of FNA protease (subtilisin BPN' containing the Y217L substitution), the PaprE-FNA catR construct was introduced in the aprE locus of the CB15-14 and CB15-14 ykfA mutant strains and the construct was amplified on Luria agar plates containing 25 µg/ml of chloramphenicol. The ykfA mutated strains and the wild type strains were grown overnight in 5 mL of Luria broth medium. 1 ml of pre-culture was used to inoculate 25 ml of 2×NB (2× Nutrient Broth, 1×SNB salts, described in WO2010/14483) in Thompson flasks at 250 rpm to test protease expression. Cell densities of whole broth diluted 20× were measured at 600 nm at hourly intervals using a SpectraMax spectrophotometer (Molecular Devices, Downington, Pa., USA). The absorbance at 600 nm was plotted as a function of time and the results are shown in FIG. 2A. The presence of the ykfA mutation resulted in higher cell growth in 2×SNB medium.

Figure 2B:
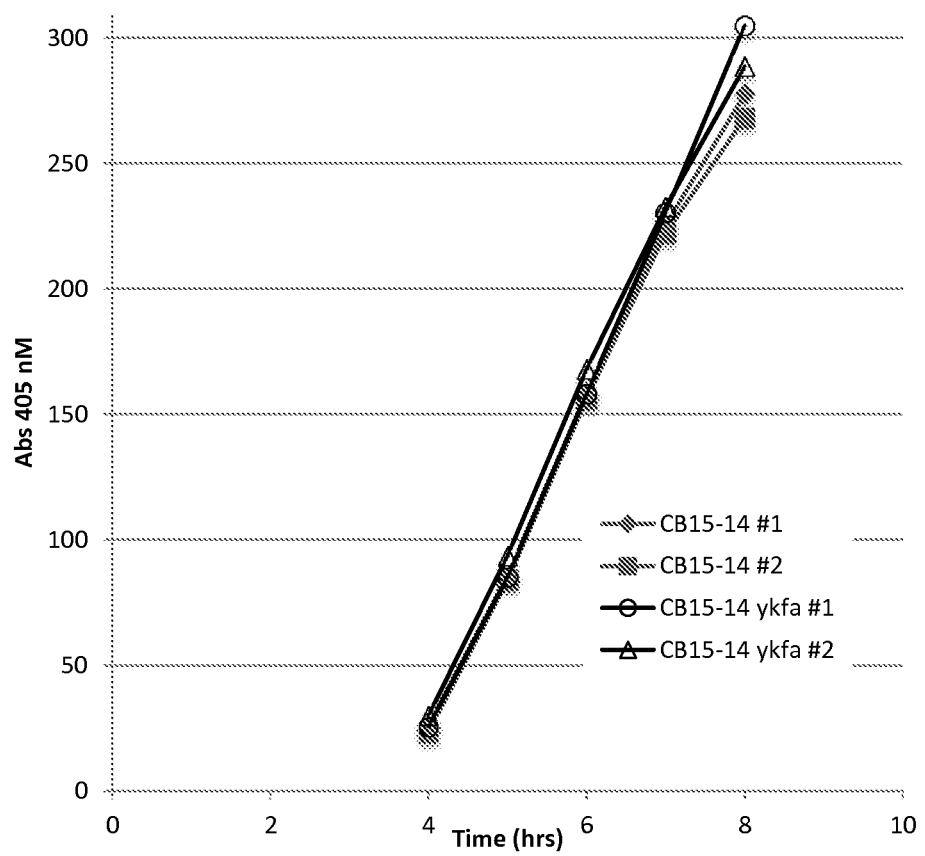
FIG. 2B shows a graph of FNA production in CB15-14 derivatives: CB15-14 #1 and #2 (control strains) and CB15-14 ykfA #1 and #2 (strains containing the ykfA mutations).

Protease expression was monitored using N-suc-AAPF-pNA substrate (from Sigma Chemical Co.) as described in WO 2010/144283. Briefly, whole broth was diluted 40× in the assay buffer (100 mM Tris, 0.005% Tween 80, pH 8.6) and 10 µl of the diluted samples were arrayed in microtiter plates. The AAPF stock was diluted and the assay buffer (100× dilution of 100 mg/ml AAPF stock in DMSO) and 190 µl of this solution were added to the microtiter plates and the absorbance of the solution was measured at 405 nm using a SpectraMax spectrophotometer (Molecular Devices, Downington, Pa., USA). The absorbance at 405 nm was plotted as a function of time and the results are shown in FIG. 2B. FNA production is increased at the later time point (8 hrs) due to the ykfA mutations.

Example 2

Figure 3A:
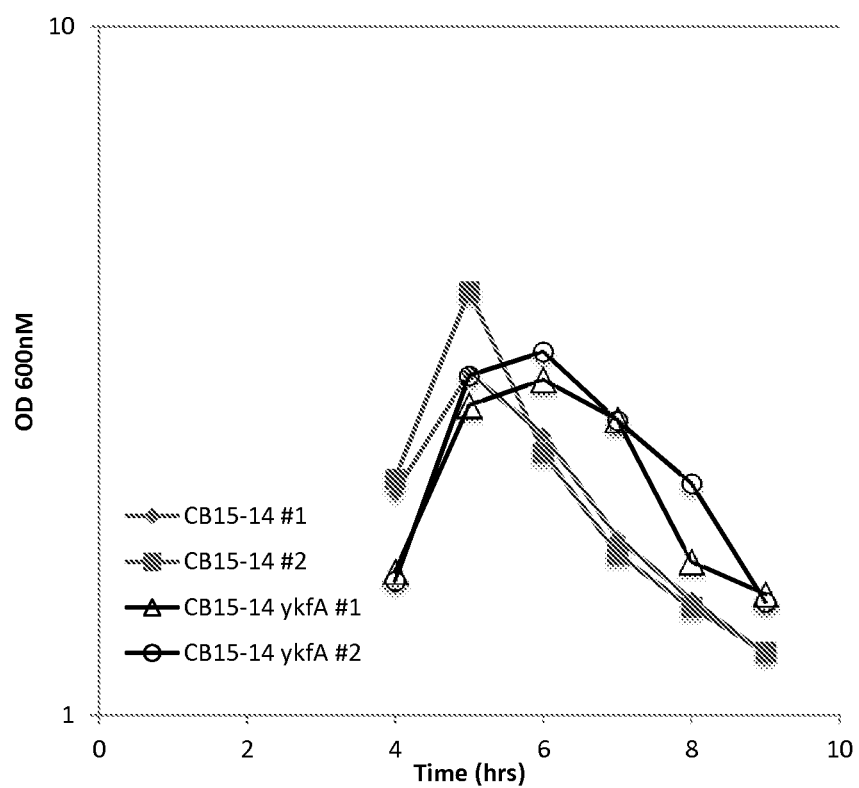
FIG. 3A shows a graph of cell densities of GFP producing CB15-14 derivatives: CB15-14 #1 and #2 (control strains) and CB15-14 ykfA #1 and #2 (strains containing the ykfA mutation). Upon the entry into stationary phase (between 4 and 6 hrs of growth), the decline in the cell growth in the ykfA mutant strains is delayed compared the control strains indicating improved cell viability due to the ykfA mutations.

Effect of ykfA Mutation on Green Fluorescence Protein Expression in *Bacillus* Species To test the effect of the ykfA mutation on expression of other proteins, the PaprE-GFP catR construct was introduced in the aprE locus of the CB15-14 and CB15-14 ykfA mutant strain and transformants were selected on Luria agar plates containing 5 µg/ml of chloramphenicol. The ykfA mutated strains and the wild type strains were grown overnight in 5 mL of Luria broth. 1 ml of pre-culture was used to inoculate 25 ml of 2×NB medium (2× nutrient broth, 1×SNB salts) in shake flasks at 37° C., 250 rpm to test the expression of green fluorescent protein (GFP). Cell densities of whole broth diluted 20× were measured at 600 nm at hourly intervals using a SpectraMax spectrophotometer (Molecular Devices, Downington, Pa., USA). The absorbance at 600 nm was plotted as a function of time and the results are shown in FIG. 3A. Upon the entry into stationary phase (between 4 and 6 hrs of growth in 2×NB), the decline in the cell growth in the ykfA mutant strains is delayed compared the control strains indicating improved cell viability due to the ykfA mutations.

Figure 3B:
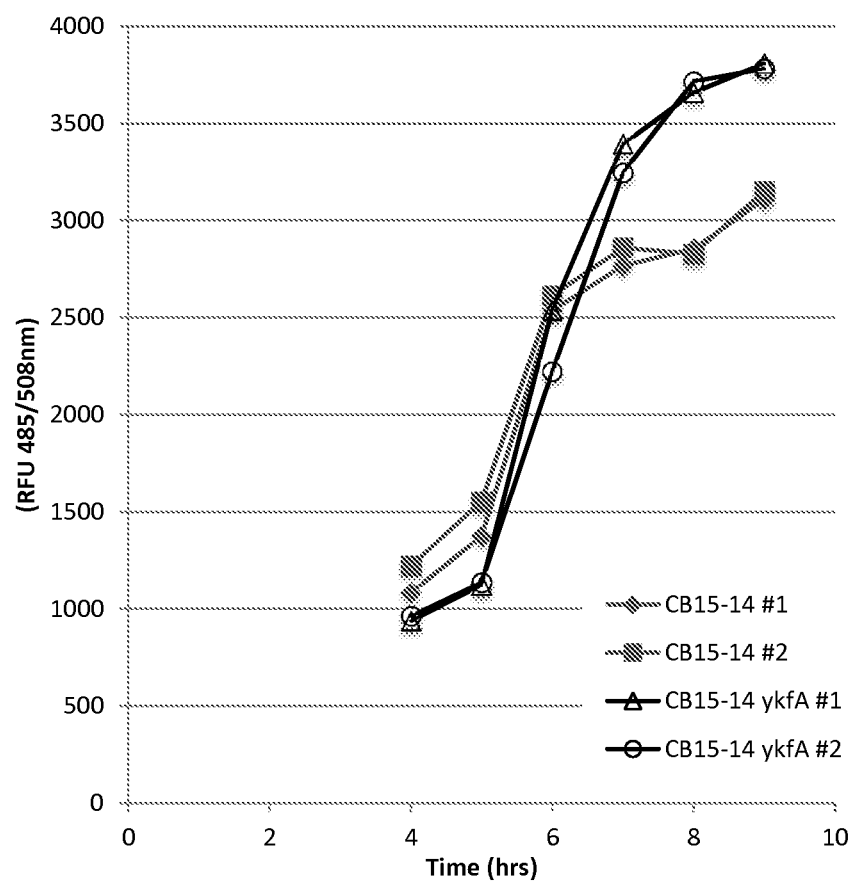
FIG. 3B shows a graph of GFP production in CB15-14 derivatives: CB15-14 #1 and #2 (control strains) and CB15-14 ykfA #1 and #2 (strains containing the ykfA mutation). The graph shows increased GFP production from 6 hrs of growth due to the ykfA mutations.

To measure GFP expression, 100 µl of culture was transferred to a 96 well microtiter plate and GFP expression was measured in a fluorescent plate reader using an excitation wavelength of 485 nm, an emission wavelength of 508 nm with a 495 nm emission cutoff filter. The relative fluorescence units (RFU) at 485/508 nm were plotted as a function of time and the results are shown in FIG. 3B. GFP production increased from 6 hrs of growth due to the ykfA mutations.

Example 3

Effect of ykfA Mutation on Beta-D-glucosidase Expression in *Bacillus* Species

Figure 4A:
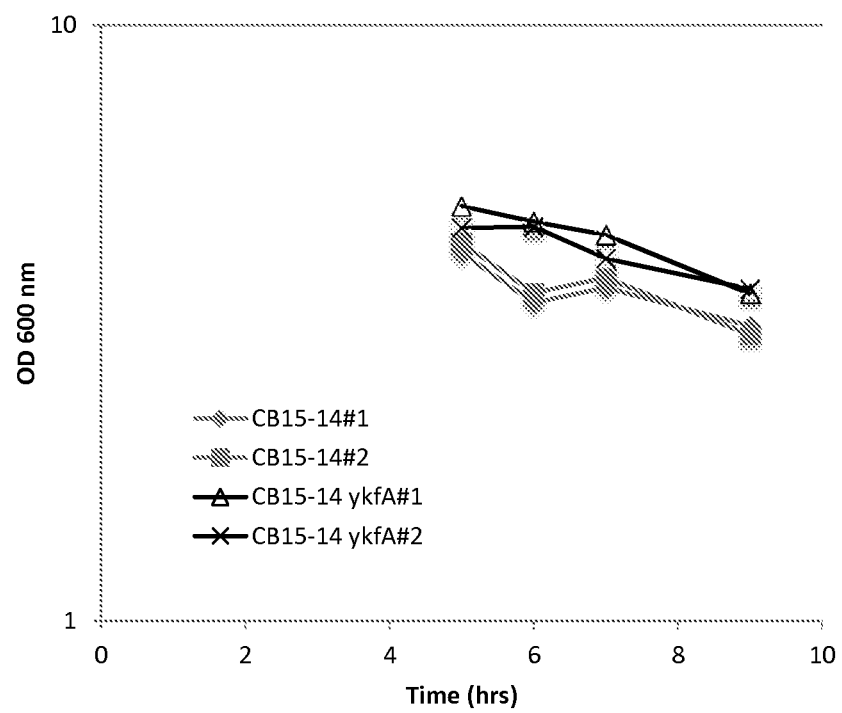
FIG. 4A shows a graph of cell densities of BglC producing CB15-14 derivatives: CB15-14 #1 and #2 (control strains) and CB15-14 ykfA #1 and #2 (strains containing ykfA mutation). Cells containing the ykfA mutations have higher cell growth, indicating improved cell viability due to the presence of the ykfA mutations.

To test the effect of the ykfA mutation on expression of beta-D-glucosidase, the PaprE-BglC catR construct was introduced in the aprE locus of the CB15-14 and CB15-14 ykfA mutant strain and transformants were selected on Luria agar plates containing 5 µg/ml of chloramphenicol. The ykfA mutated strains and the wild type strains were grown overnight in 5 mL of Luria broth. 1 ml of pre-culture was used to inoculate 25 ml of 2×NB medium (2× nutrient broth, 1× SNB salts) in shake flasks at 37° C., 250 rpm to test the expression of the secreted beta-D-glucosidase. Cell densities of whole broth diluted 20× were measured at 600 nm at hourly intervals using a SpectraMax spectrophotometer (Molecular Devices, Downington, Pa., USA). The absorbance at 600 nm was plotted as a function of time and the results are shown in FIG. 4A. Cells containing the ykfA mutations have higher cell growth, indicating improved cell viability due to the presence of the ykfA mutations.

Figure 4B:
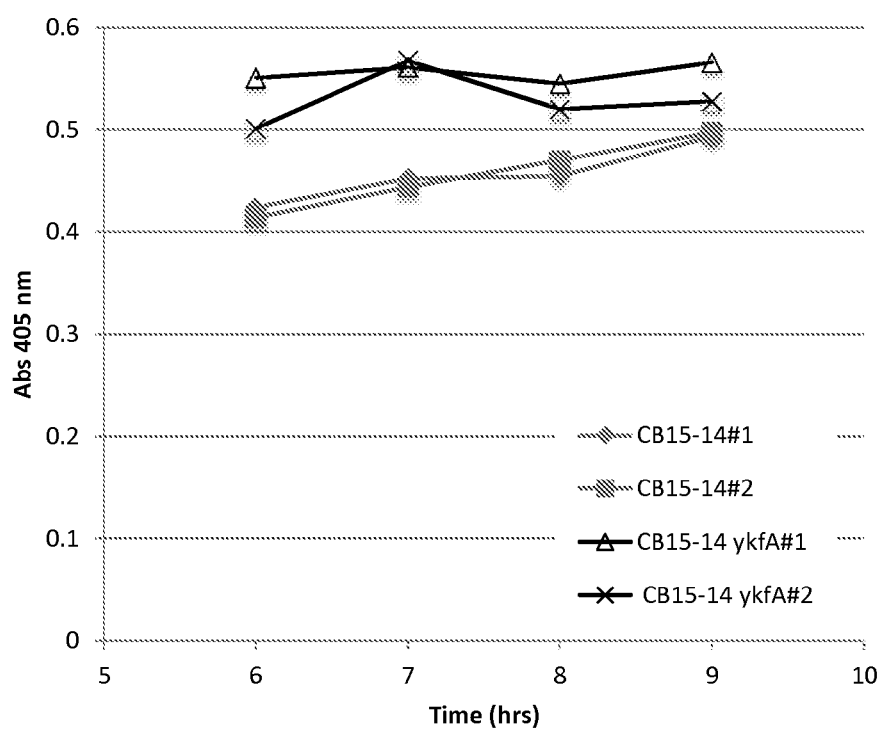
FIG. 4B shows a graph of BglC production in CB15-14 derivatives: CB15-14 #1 and #2 (control strains) and CB15-14 ykfA #1 and #2 (strains containing ykfA mutation). The graph shows increased BglC production for all the time points due to the presence of the ykfA mutations.

Beta-D-glucosidase expression was monitored using 4-Nitrophenyl-β-D-cellobioside substrate (Sigma Chemicals, St. Louis, Mo., USA, Cat. #N57590). The substrate was dissolved in 1 ml of DMSO to create the stock solution at 100 mg/ml. The working substrate solution was made by diluting 35 µl of the stock solution in 10 ml of assay buffer (100 mM Tris, 0.005% Tween 80, pH 8.6). Forty microliters of each culture was transferred to a 96 well microtiter plate and 180 μl of the working substrate solution was added to each well. The microtiter plate was incubated at room temperature for 5 hours and at the end of the incubation period, the absorbance of the solution was measured at 405 nm using a SpectraMax spectrophotometer (Molecular Devices, Downington, Pa., USA). The absorbance at 405 nm was plotted as a function of time and the results are shown in FIG. 4B. BgIC production increased for all the time points due to the presence of the ykfA mutations.

In view of the data described above, it is clear that modifying activity of a protein encoded by the ykf operon (e.g., the ykfA gene) in a Gram positive bacterial cell (i.e., as compared to a parental cell) results in increased expression of a protein of interest as compared to the parental cell when cultured under the same, or essentially the same, culture conditions.

Although the foregoing compositions and methods have been described in some detail by way of illustration and example for purposes of clarity of understanding, it is readily apparent to those of ordinary skill in the art in light of the teachings herein that certain changes and modifications may be made thereto without departing from the spirit or scope of the appended claims.

Accordingly, the preceding merely illustrates the principles of the present compositions and methods. It will be appreciated that those skilled in the art will be able to devise various arrangements which, although not explicitly described or shown herein, embody the principles of the present compositions and methods and are included within its spirit and scope. Furthermore, all examples and conditional language recited herein are principally intended to aid the reader in understanding the principles of the present compositions and methods and the concepts contributed by the inventors to furthering the art, and are to be construed as being without limitation to such specifically recited examples and conditions. Moreover, all statements herein reciting principles, aspects, and embodiments of the present compositions and methods as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present compositions and methods, therefore, is not intended to be limited to the embodiments shown and described herein.

SEQUENCES

SEQ ID NO: 1-ykfA wildtype nucleotide sequence
atgaaaggagtgttttcgttgaattacaagccgaaagcgttgaacaaggg tgatacagtcggagtgatcgcgcccgcaagtccgccggatccaaaaaagc ttgacaccgcgcttttattttagaagagctcggtcttcaggtgaagttg ggcaaggcgctgaaaaaccagcacggctatttagcgggacaggatgatga gcggctggcggatctccatgagatgttcagagacgatgaggtaaaagcag tgttgtgcgcatgcgggggttttgggacaggacgtatcgccgcgggcatt gatttcagcttgatccgcaaacaccctaaaatcttttggggatacagcga tattacgttttacatactgccattcatcaaaacacaggtcttgtcactt tccatggcccgatgctcagcacggatattggccttgacgacgttcacccg ctgacaaaagcgtcatataagcagctcttccaggagacggaattcaccta tacagaagagctttctccgctgaccgagcttgttcctggaaaagcggaag gcgagcttgtcgggggaaatctgtctttgctgacgtctacactgggcacg ccatttgaaattgatacgagaggaaagcttctgtttattgaagatattga cgaggagccttatcaaatcgaccggatgctgaatcagctgaaaatggggg ggaagctgacggacgcggcgggaattctagtttgtgattttcacaattgt gtcccggtgaagcgagagaagtctctctcgcttgagcaggtgctggaaga ctatattatttctgcgggcaggcctgctctgagaggatttaaaatcggcc actgctcgccaagtattgccgttccgatcggtgcgaaagctgctatgaat acagcagaaaaaacagccgtaatagaggcgggcgtttcagaaggggcgct gaagacatga SEQ ID NO: 2-YkfA wild type protein sequence
MKGVFSLNYKPKALNKGDTVGVIAPASPPDPKKLDTALLFLEELGLQVKL

GKALKNQHGYLAGQDDERLADLHEMFRDDEVKAVLCACGGFGTGRIAAGI

DFSLIRKHPKIFWGYSDITFLHTAIHQNTGLVTFHGPMLSTDIGLDDVHP

LTKASYKQLFQETEFTYTEELSPLTELVPGKAEGELVGGNLSLLTSTLGT

PFEIDTRGKLLFIEDIDEEPYQIDRMLNQLKMGGKLTDAAGILVCDFHNC

VPVKREKSLSLEQVLEDYIISAGRPALRGFKIGHCSPSIAVPIGAKAAMN

TAEKTAVIEAGVSEGALKT

SEQ ID NO: 3-ykfA mutant nucleotide sequence
atgaaaggagtgttttcgttgaattacaagccgaaagcgttgaacaaggg tgatacagtcggagtgatcgcgcccgcaagtccgccggatccaaaaaagc ttgacaccgcgcttttattttagaagagctcggtcttcaggtgaagttg ggcaaggcgctgaaaaaccagcacggctatttagcgggacaggatgatga gcggctggcggatctccatgagatgttcagagacgatgaggtaaaagcag tgttgtgcgcatgcgggggttttgggacaggacgtatcgccgcgggcatt gatttcagcttgatccgcaaacaccctaaaatcttttggggatacagcga tattacgttttacatactgccattcatcaaaacacaggtcttgtcactt tccatggcccgatgctcagcacggatattggccttgacgacgttcacccg ctgacaaaagcgtcatataagcagctcttccaggagacggaattcaccta tacagaagagctttctccgctgaccgagctgttcctggaaaagcggaagg cgagcttgtcgggggaaatctgtctttgctgacgtctacactgggcacgc catttgaaattgatacgagaggaaagcttctgtttattgaagatattgac gaggagccttatcaaatcgaccggatgctgaatcagctgaaaatggggg gaagctgacggacgcggcgggaattctagtttgtgattttcacaattgtg tcctgctcaagcgagagaagtctctctcgcttgagcaggtgctggaagac tatattatttctgcgggcaggcctgctctgagaggatttaaaatcggcca ctgctcgccaagtattgccgttccgatcggtgcgaaagctgctatgaata cagcagaaaaaacagccgtaatagaggcgggcgtttcagaaggggcgctg aagacatga

SEQUENCES

SEQ ID NO: 4::YkfA mutant protein sequence
(with P252L and V253L alterations)
MKGVFSLNYKPKALNKGDTVGVIAPASPPDPKKLDTALLFLEELGLQVKL

GKALKNQHGYLAGQDDERLADLHEMFRDDEVKAVLCACGGFGTGRIAAGI

DFSLIRKHPKIFWGYSDITFLHTAIHQNTGLVTFHGPMLSTDIGLDDVHP

LTKASYKQLFQETEFTYTEELSPLTELVPGKAEGELVGGNLSLLTSTLGT

PFEIDTRGKLLFIEDIDEEPYQIDRMLNQLKMGGKLTDAAGILVCDFHNC

VLLKREKSLSLEQVLEDYIISAGRPALRGFKIGHCSPSIAVPIGAKAAMN

TAEKTAVIEAGVSEGALKT

SEQ ID NO: 5::FNA protein sequence
(with pro-domain)
AQSVPYGVSQIKAPALHSQGYTGSNVKVAVIDSGIDSSHPDLKVA

GGASMVPSETNPFQDNNSHGTHVAGTVAALNNSIGVLGVAPSAS

LYAVKVLGADGSGQYSWIINGIEWAIANNMDVINMSLGGPSGSAA

LKAAVDKAVASGVVVVAAAGNEGTSGSSSTVGYPGKYPSVIAVG

AVDSSNQRASFSSVGPELDVMAPGVSIQSTLPGNKYGALNGTSM

ASPHVAGAAALILSKHPNWTNTQVRSSLENTTTKLGDSFYYGKGL

INVQAAAQ

SEQ ID NO: 6::GFP protein sequence
VNRNVLKNTGLKEIMSAKASVEGIVNNHVFSMEGFGKGNVLFGN

QLMQIRVTKGGPLPFAFDIVSIAFQYGNRTFTKYPDDIADYFVQSF

PAGFFYERNLRFEDGAIVDIRSDISLEDDKFHYKVEYRGNGFPSN

GPVMQKAILGMEPSFEVVYMNSGVLVGEVDLVYKLESGNYYSCH

MKTFYRSKGGVKEFPEYHFIHHRLEKTYVEEGSFVEQHETAIAQL

TTIGKPLGSLHEWV

SEQ ID NO: 7::BglC protein sequence
AAGTKTPVAKNGQLSIKGTQLVNRDGKAVQLKGISSHGLQWYGE

YVNKDSLKWLRDDWGITVFRAAMYTADGGYIDNPSVKNKVKEAV

EAAKELGIYVIIDWHILNDGNPNQNKEKAKEFFKEMSSLYGNTPN

VIYEIANEPNGDVNWKRDIKPYAEEVISVIRKNDPDNIIIVGTGTW

SQDVNDAADDQLKDANVMYALHFYAGTHGQFLRDKANYALSKGA

PIFVTEWGTSDASGNGGVFLDQSREWLKYLDSKTISWVNWNLSD

KQESSSALKPGASKTGGWRLSDLSASGTFVRENILGTKDSTKDIP

ETPSKDKPTQENGISVQYRAGDGSMNSNQIRPQLQIKNNGNTTV

DLKDVTARYWYKAKNKGQNFDCDYAQIGCGNVTHKFVTLHKPKQ

GADTYLELGFKNGTLAPGASTGNIQLRLHNDDWSNYAQSGDYSF

FKSNTFKTTKKITLYDQGKLIWGTEPN

---

The invention claimed is:

1. A method for increasing expression of a protein of interest from a *Bacillus* sp. bacterial cell comprising:
   a) obtaining an altered *Bacillus* sp. bacterial cell capable of producing a protein of interest, wherein said altered *Bacillus* cell comprises a genetic alteration of a gene encoding a YkfA protein comprising SEQ ID NO: 2, wherein the genetic alteration results in an amino acid substitution at amino acid residue 252 or 253 of SEQ ID NO: 2; and
   b) culturing said altered *Bacillus* sp. bacterial cell under conditions such that said protein of interest is expressed by said altered *Bacillus* sp. bacterial cell, wherein expression of said protein of interest is increased in said altered *Bacillus* sp. bacterial cell compared to the expression of said protein of interest in a corresponding unaltered *Bacillus* sp. bacterial cell grown under essentially the same culture conditions.

2. The method of claim 1, wherein said ykfA gene is at least 95% identical to SEQ ID NO: 1, and encodes a YkfA protein comprising an amino acid substitution at amino acid residue 252 or 253 of SEQ ID NO: 2.

3. The method of claim 1, wherein said genetic alteration results in an amino acid substitution at a position corresponding to amino acids 252 and 253 of SEQ ID NO: 2.

4. The method of claim 1, wherein said genetic alteration results in a P to L alteration in an amino acid at a position corresponding to amino acid 252 of SEQ ID NO: 2.

5. The method of claim 1, wherein said genetic alteration results in a V to L alteration in an amino acid at a position corresponding to amino acid 253 of SEQ ID NO: 2.

6. The method of claim 1, wherein said genetic alteration results in a P to L alteration in an amino acid position corresponding to amino acid 252 and in a V to L alteration in an amino acid position corresponding to amino acid 253 of SEQ ID NO: 2.

7. The method of claim 1, wherein said protein of interest is an enzyme.

8. The method of claim 1, wherein said protein of interest is a protease.

9. The method of claim 1, further comprising recovering said protein of interest.

10. An altered *Bacillus* sp. bacterial cell, wherein said altered *Bacillus* cell comprises a genetic alteration of a gene encoding a YkfA protein comprising SEQ ID NO: 2, wherein the genetic alteration results in an amino acid substitution at amino acid residue Pro-252 or Val-253 of SEQ ID NO: 2, wherein the altered *Bacillus* cell produces an increased amount of an endogenous or heterologous protein of interest relative to an unaltered parental *Bacillus* cell grown under essentially the same culture conditions.

11. A polynucleotide comprising a variant sequence derived from a *Bacillus* sp. ykfA gene, wherein said variant sequence is at least 960 nucleotides in length, is at least 95% identical SEQ ID NO:1 encoding a YkfA protein of SEQ ID NO: 2, and comprises at least one genetic alteration at a nucleotide position in the ykfA gene that results in a substitution in an amino acid at a position corresponding to amino acid 252 or 253 of SEQ ID NO: 2.

12. The polynucleotide of claim 11, wherein said genetic alteration results in an amino acid substitution at a position corresponding to amino acid 252 and 253 of SEQ ID NO: 2.

13. A vector comprising the polynucleotide sequence of claim 11.

14. The vector of claim 13, wherein said vector is a targeting vector designed to introduce the at least one mutation in said polynucleotide sequence into the corresponding location in the ykf operon of a *Bacillus* sp. bacterial cell by homologous recombination when transformed into said *Bacillus* sp. bacterial cell.

15. A method for enhancing expression of a protein of interest in a *Bacillus* sp. bacterial cell comprising:
   a) transforming a parental *Bacillus* sp. bacterial cell with the vector of claim 14;
   b) allowing homologous recombination of said vector and the corresponding region in the ykf operon of said parental *Bacillus* sp. bacterial cell to produce an altered *Bacillus* sp. bacterial cell; and
   c) growing said altered *Bacillus* sp. bacterial cell under conditions suitable for the expression of said protein of interest,
   wherein the production of said protein of interest is increased in the altered *Bacillus* sp. bacterial cell as compared to said *Bacillus* sp. bacterial cell prior to said transformation in step.

* * * * *

SEQUENCE LISTING

```
<160> NUMBER OF SEQ ID NOS: 7

<210> SEQ ID NO 1
<211> LENGTH: 960
<212> TYPE: DNA
<213> ORGANISM: Bacillus subtilis
<220> FEATURE:
<221> NAME/KEY: misc_feature
<223> OTHER INFORMATION: ykfA wildtype nucleotide sequence

<400> SEQUENCE: 1
atgaaaggag tgttttcgtt gaattacaag ccgaaagcgt tgaacaaggg tgatacagtc     60
ggagtgatcg cgcccgcaag tccgccggat ccaaaaaagc ttgacaccgc gctttttattt   120 ttagaagagc tcggtcttca ggtgaagttg gcaaggcgc tgaaaaacca gcacggctat    180
ttagcgggac aggatgatga gcggctggcg gatctccatg agatgttcag agacgatgag   240
gtaaaagcag tgttgtgcgc atgcgggggt tttgggacag acgtatcgc cgcgggcatt    300 gatttcagct tgatccgcaa acaccctaaa atctttggg gatacagcga tattacgttt   360
ttacatactg ccattcatca aaacacaggt cttgtcactt tccatggccc gatgctcagc   420
acggatattg ccttgacga cgttcacccg ctgacaaaag cgtcatataa gcagctcttc   480
caggagacgg aattcaccta tacagaagag ctttctccgc tgaccgagct tgttcctgga   540
aaagcggaag cgagcttgt cggggaaat ctgtctttgc tgacgtctac actgggcacg   600
ccatttgaaa ttgatacgag aggaaagctt ctgtttattg aagatattga cgaggagcct   660
```

```
tatcaaatcg accggatgct gaatcagctg aaaatggggg ggaagctgac ggacgcggcg    720
ggaattctag tttgtgattt tcacaattgt gtcccggtga agcgagagaa gtctctctcg    780
cttgagcagg tgctggaaga ctatattatt tctgcgggca ggcctgctct gagaggattt    840
aaaatcggcc actgctcgcc aagtattgcc gttccgatcg gtgcgaaagc tgctatgaat    900
acagcagaaa aaacagccgt aatagaggcg ggcgtttcag aaggggcgct gaagacatga    960
```

<210> SEQ ID NO 2
<211> LENGTH: 319
<212> TYPE: PRT
<213> ORGANISM: Bacillus subtilis
<220> FEATURE:
<221> NAME/KEY: misc_feature
<223> OTHER INFORMATION: YkfA wild type protein sequence

<400> SEQUENCE: 2

```
Met Lys Gly Val Phe Ser Leu Asn Tyr Lys Pro Lys Ala Leu Asn Lys
1               5                   10                  15

Gly Asp Thr Val Gly Val Ile Ala Pro Ala Ser Pro Pro Asp Pro Lys
            20                  25                  30

Lys Leu Asp Thr Ala Leu Leu Phe Leu Glu Glu Leu Gly Leu Gln Val
        35                  40                  45

Lys Leu Gly Lys Ala Leu Lys Asn Gln His Gly Tyr Leu Ala Gly Gln
    50                  55                  60

Asp Asp Glu Arg Leu Ala Asp Leu His Glu Met Phe Arg Asp Asp Glu
65                  70                  75                  80

Val Lys Ala Val Leu Cys Ala Cys Gly Gly Phe Gly Thr Gly Arg Ile
                85                  90                  95

Ala Ala Gly Ile Asp Phe Ser Leu Ile Arg Lys His Pro Lys Ile Phe
            100                 105                 110

Trp Gly Tyr Ser Asp Ile Thr Phe Leu His Thr Ala Ile His Gln Asn
        115                 120                 125

Thr Gly Leu Val Thr Phe His Gly Pro Met Leu Ser Thr Asp Ile Gly
    130                 135                 140

Leu Asp Asp Val His Pro Leu Thr Lys Ala Ser Tyr Lys Gln Leu Phe
145                 150                 155                 160

Gln Glu Thr Glu Phe Thr Tyr Thr Glu Glu Leu Ser Pro Leu Thr Glu
                165                 170                 175

Leu Val Pro Gly Lys Ala Glu Gly Glu Leu Val Gly Gly Asn Leu Ser
            180                 185                 190

Leu Leu Thr Ser Thr Leu Gly Thr Pro Phe Glu Ile Asp Thr Arg Gly
        195                 200                 205

Lys Leu Leu Phe Ile Glu Asp Ile Asp Glu Glu Pro Tyr Gln Ile Asp
    210                 215                 220

Arg Met Leu Asn Gln Leu Lys Met Gly Gly Lys Leu Thr Asp Ala Ala
225                 230                 235                 240

Gly Ile Leu Val Cys Asp Phe His Asn Cys Val Pro Val Lys Arg Glu
                245                 250                 255

Lys Ser Leu Ser Leu Glu Gln Val Leu Glu Asp Tyr Ile Ile Ser Ala
            260                 265                 270

Gly Arg Pro Ala Leu Arg Gly Phe Lys Ile Gly His Cys Ser Pro Ser
        275                 280                 285

Ile Ala Val Pro Ile Gly Ala Lys Ala Ala Met Asn Thr Ala Glu Lys
    290                 295                 300

Thr Ala Val Ile Glu Ala Gly Val Ser Glu Gly Ala Leu Lys Thr
```

<210> SEQ ID NO 3
<211> LENGTH: 960
<212> TYPE: DNA
<213> ORGANISM: Artificial Sequence
<220> FEATURE:
<223> OTHER INFORMATION: Synthetic: ykfA mutant nucleotide sequence

<400> SEQUENCE: 3

| | | | | | |
|---|---|---|---|---|---|
| atgaaaggag | tgttttcgtt | gaattacaag | ccgaaagcgt | tgaacaaggg | tgatacagtc | 60 |
| ggagtgatcg | cgcccgcaag | tccgccggat | ccaaaaaagc | ttgacaccgc | gcttttattt | 120 |
| ttagaagagc | tcggtcttca | ggtgaagttg | ggcaaggcgc | tgaaaaacca | gcacggctat | 180 |
| ttagcgggac | aggatgatga | gcggctggcg | gatctccatg | agatgttcag | agacgatgag | 240 |
| gtaaaagcag | tgttgtgcgc | atgcgggggt | tttgggacag | gacgtatcgc | cgcgggcatt | 300 |
| gatttcagct | tgatccgcaa | acaccctaaa | atcttttggg | gatacagcga | tattacgttt | 360 |
| ttacatactg | ccattcatca | aaacacaggt | cttgtcactt | tccatggccc | gatgctcagc | 420 |
| acggatattg | ccttgacga | cgttcacccg | ctgacaaaag | cgtcatataa | gcagctcttc | 480 |
| caggagacgg | aattcaccta | tacagaagag | ctttctccgc | tgaccgagct | tgttcctgga | 540 |
| aaagcggaag | gcgagcttgt | cggggggaaat | ctgtctttgc | tgacgtctac | actgggcacg | 600 |
| ccatttgaaa | ttgatacgag | aggaaagctt | ctgtttattg | aagatattga | cgaggagcct | 660 |
| tatcaaatcg | accggatgct | gaatcagctg | aaaatggggg | ggaagctgac | ggacgcggcg | 720 |
| ggaattctag | tttgtgattt | tcacaattgt | gtcctgctca | agcgagagaa | gtctctctcg | 780 |
| cttgagcagg | tgctggaaga | ctatattatt | tctgcgggca | ggcctgctct | gagaggattt | 840 |
| aaaatcggcc | actgctcgcc | aagtattgcc | gttccgatcg | gtgcgaaagc | tgctatgaat | 900 |
| acagcagaaa | aaacagccgt | aatagaggcg | ggcgtttcag | aaggggcgct | gaagacatga | 960 |

<210> SEQ ID NO 4
<211> LENGTH: 319
<212> TYPE: PRT
<213> ORGANISM: Artificial Sequence
<220> FEATURE:
<223> OTHER INFORMATION: Synthetic: YkfA mutant protein sequence (with P252L and V253L alterations)

<400> SEQUENCE: 4

Met Lys Gly Val Phe Ser Leu Asn Tyr Lys Pro Lys Ala Leu Asn Lys
1               5                   10                  15

Gly Asp Thr Val Gly Val Ile Ala Pro Ala Ser Pro Pro Asp Pro Lys
            20                  25                  30

Lys Leu Asp Thr Ala Leu Leu Phe Leu Glu Glu Leu Gly Leu Gln Val
        35                  40                  45

Lys Leu Gly Lys Ala Leu Lys Asn Gln His Gly Tyr Leu Ala Gly Gln
    50                  55                  60

Asp Asp Glu Arg Leu Ala Asp Leu His Glu Met Phe Arg Asp Asp Glu
65                  70                  75                  80

Val Lys Ala Val Leu Cys Ala Cys Gly Gly Phe Gly Thr Gly Arg Ile
                85                  90                  95

Ala Ala Gly Ile Asp Phe Ser Leu Ile Arg Lys His Pro Lys Ile Phe
            100                 105                 110

Trp Gly Tyr Ser Asp Ile Thr Phe Leu His Thr Ala Ile His Gln Asn
        115                 120                 125

```
Thr Gly Leu Val Thr Phe His Gly Pro Met Leu Ser Thr Asp Ile Gly
130                 135                 140

Leu Asp Asp Val His Pro Leu Thr Lys Ala Ser Tyr Lys Gln Leu Phe
145                 150                 155                 160

Gln Glu Thr Glu Phe Thr Tyr Thr Glu Leu Ser Pro Leu Thr Glu
                165                 170                 175

Leu Val Pro Gly Lys Ala Glu Gly Leu Val Gly Gly Asn Leu Ser
                180                 185                 190

Leu Leu Thr Ser Thr Leu Gly Thr Pro Phe Glu Ile Asp Thr Arg Gly
            195                 200                 205

Lys Leu Leu Phe Ile Glu Asp Ile Asp Glu Pro Tyr Gln Ile Asp
210                 215                 220

Arg Met Leu Asn Gln Leu Lys Met Gly Gly Lys Leu Thr Asp Ala Ala
225                 230                 235                 240

Gly Ile Leu Val Cys Asp Phe His Asn Cys Val Leu Lys Arg Glu
                245                 250                 255

Lys Ser Leu Ser Leu Glu Gln Val Leu Glu Asp Tyr Ile Ile Ser Ala
            260                 265                 270

Gly Arg Pro Ala Leu Arg Gly Phe Lys Ile Gly His Cys Ser Pro Ser
            275                 280                 285

Ile Ala Val Pro Ile Gly Ala Lys Ala Ala Met Asn Thr Ala Glu Lys
290                 295                 300

Thr Ala Val Ile Glu Ala Gly Val Ser Glu Gly Ala Leu Lys Thr
305                 310                 315

<210> SEQ ID NO 5
<211> LENGTH: 275
<212> TYPE: PRT
<213> ORGANISM: Artificial Sequence
<220> FEATURE:
<223> OTHER INFORMATION: Synthetic: FNA protein sequence (with pro-
      domain)

<400> SEQUENCE: 5

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175
```

```
Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Leu Asn Gly Thr Ser Met Ala Ser
210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 6
<211> LENGTH: 238
<212> TYPE: PRT
<213> ORGANISM: Artificial Sequence
<220> FEATURE:
<223> OTHER INFORMATION: Synthetic: GFP protein sequence

<400> SEQUENCE: 6

Val Asn Arg Asn Val Leu Lys Asn Thr Gly Leu Lys Glu Ile Met Ser
1               5                   10                  15

Ala Lys Ala Ser Val Glu Gly Ile Val Asn Asn His Val Phe Ser Met
            20                  25                  30

Glu Gly Phe Gly Lys Gly Asn Val Leu Phe Gly Asn Gln Leu Met Gln
        35                  40                  45

Ile Arg Val Thr Lys Gly Gly Pro Leu Pro Phe Ala Phe Asp Ile Val
    50                  55                  60

Ser Ile Ala Phe Gln Tyr Gly Asn Arg Thr Phe Thr Lys Tyr Pro Asp
65                  70                  75                  80

Asp Ile Ala Asp Tyr Phe Val Gln Ser Phe Pro Ala Gly Phe Tyr
                85                  90                  95

Glu Arg Asn Leu Arg Phe Glu Asp Gly Ala Ile Val Asp Ile Arg Ser
            100                 105                 110

Asp Ile Ser Leu Glu Asp Asp Lys Phe His Tyr Lys Val Glu Tyr Arg
        115                 120                 125

Gly Asn Gly Phe Pro Ser Asn Gly Pro Val Met Gln Lys Ala Ile Leu
    130                 135                 140

Gly Met Glu Pro Ser Phe Glu Val Val Tyr Met Asn Ser Gly Val Leu
145                 150                 155                 160

Val Gly Glu Val Asp Leu Val Tyr Lys Leu Glu Ser Gly Asn Tyr Tyr
                165                 170                 175

Ser Cys His Met Lys Thr Phe Tyr Arg Ser Lys Gly Gly Val Lys Glu
            180                 185                 190

Phe Pro Glu Tyr His Phe Ile His His Arg Leu Glu Lys Thr Tyr Val
        195                 200                 205

Glu Glu Gly Ser Phe Val Glu Gln His Glu Thr Ala Ile Ala Gln Leu
    210                 215                 220

Thr Thr Ile Gly Lys Pro Leu Gly Ser Leu His Glu Trp Val
225                 230                 235

<210> SEQ ID NO 7
```

-continued

```
<211> LENGTH: 471
<212> TYPE: PRT
<213> ORGANISM: Artificial Sequence
<220> FEATURE:
<223> OTHER INFORMATION: Synthetic: BglC protein sequence

<400> SEQUENCE: 7
```

Ala Ala Gly Thr Lys Thr Pro Val Ala Lys Asn Gly Gln Leu Ser Ile
1               5                   10                  15

Lys Gly Thr Gln Leu Val Asn Arg Asp Gly Lys Ala Val Gln Leu Lys
            20                  25                  30

Gly Ile Ser Ser His Gly Leu Gln Trp Tyr Gly Glu Tyr Val Asn Lys
        35                  40                  45

Asp Ser Leu Lys Trp Leu Arg Asp Asp Trp Gly Ile Thr Val Phe Arg
    50                  55                  60

Ala Ala Met Tyr Thr Ala Asp Gly Gly Tyr Ile Asp Asn Pro Ser Val
65                  70                  75                  80

Lys Asn Lys Val Lys Glu Ala Val Glu Ala Lys Glu Leu Gly Ile
                85                  90                  95

Tyr Val Ile Ile Asp Trp His Ile Leu Asn Asp Gly Asn Pro Asn Gln
                100                 105                 110

Asn Lys Glu Lys Ala Lys Glu Phe Lys Glu Met Ser Ser Leu Tyr
            115                 120                 125

Gly Asn Thr Pro Asn Val Ile Tyr Glu Ile Ala Asn Glu Pro Asn Gly
        130                 135                 140

Asp Val Asn Trp Lys Arg Asp Ile Lys Pro Tyr Ala Glu Glu Val Ile
145                 150                 155                 160

Ser Val Ile Arg Lys Asn Asp Pro Asp Asn Ile Ile Val Gly Thr
                165                 170                 175

Gly Thr Trp Ser Gln Asp Val Asn Asp Ala Ala Asp Gln Leu Lys
            180                 185                 190

Asp Ala Asn Val Met Tyr Ala Leu His Phe Tyr Ala Gly Thr His Gly
        195                 200                 205

Gln Phe Leu Arg Asp Lys Ala Asn Tyr Ala Leu Ser Lys Gly Ala Pro
    210                 215                 220

Ile Phe Val Thr Glu Trp Gly Thr Ser Asp Ala Ser Gly Asn Gly Gly
225                 230                 235                 240

Val Phe Leu Asp Gln Ser Arg Glu Trp Leu Lys Tyr Leu Asp Ser Lys
                245                 250                 255

Thr Ile Ser Trp Val Asn Trp Asn Leu Ser Asp Lys Gln Glu Ser Ser
            260                 265                 270

Ser Ala Leu Lys Pro Gly Ala Ser Lys Thr Gly Gly Trp Arg Leu Ser
        275                 280                 285

Asp Leu Ser Ala Ser Gly Thr Phe Val Arg Glu Asn Ile Leu Gly Thr
    290                 295                 300

Lys Asp Ser Thr Lys Asp Ile Pro Glu Thr Pro Ser Lys Asp Lys Pro
305                 310                 315                 320

Thr Gln Glu Asn Gly Ile Ser Val Gln Tyr Arg Ala Gly Asp Gly Ser
                325                 330                 335

Met Asn Ser Asn Gln Ile Arg Pro Gln Leu Gln Ile Lys Asn Asn Gly
            340                 345                 350

Asn Thr Thr Val Asp Leu Lys Asp Val Thr Ala Arg Tyr Trp Tyr Lys
        355                 360                 365

Ala Lys Asn Lys Gly Gln Asn Phe Asp Cys Asp Tyr Ala Gln Ile Gly
    370                 375                 380

```
Cys Gly Asn Val Thr His Lys Phe Val Thr Leu His Lys Pro Lys Gln
385                 390                 395                 400

Gly Ala Asp Thr Tyr Leu Glu Leu Gly Phe Lys Asn Gly Thr Leu Ala
                405                 410                 415

Pro Gly Ala Ser Thr Gly Asn Ile Gln Leu Arg Leu His Asn Asp Asp
            420                 425                 430

Trp Ser Asn Tyr Ala Gln Ser Gly Asp Tyr Ser Phe Phe Lys Ser Asn
        435                 440                 445

Thr Phe Lys Thr Thr Lys Lys Ile Thr Leu Tyr Asp Gln Gly Lys Leu
    450                 455                 460

Ile Trp Gly Thr Glu Pro Asn
465                 470
```